(12) United States Patent
Minomi et al.

(10) Patent No.: US 10,047,111 B2
(45) Date of Patent: *Aug. 14, 2018

(54) RNA INTERFERENCE AGENTS FOR GST-PI GENE MODULATION

(71) Applicant: Nitto Denko Corporation, Osaka (JP)

(72) Inventors: Kenjirou Minomi, Osaka (JP); Hirokazu Takahashi, Osaka (JP); Erika Terada, Osaka (JP); Jens Harborth, Carlsbad, CA (US); Jun Zhang, San Diego, CA (US); Mohammad Ahmadian, Carlsbad, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/979,574

(22) Filed: Dec. 28, 2015

(65) Prior Publication Data

US 2016/0208265 A1    Jul. 21, 2016

Related U.S. Application Data

(60) Provisional application No. 62/266,664, filed on Dec. 13, 2015, provisional application No. 62/184,239, filed on Jun. 24, 2015.

(30) Foreign Application Priority Data

Dec. 26, 2014 (JP) ................ 2014-266198

(51) Int. Cl.
| | | |
|---|---|---|
| *C12N 15/113* | (2010.01) | |
| *C07H 21/02* | (2006.01) | |
| *C07H 21/04* | (2006.01) | |
| *C07F 9/6533* | (2006.01) | |
| *C12Q 1/02* | (2006.01) | |
| *G01N 33/58* | (2006.01) | |
| *A61K 31/713* | (2006.01) | |

(52) U.S. Cl.
CPC .......... *C07F 9/6533* (2013.01); *C12N 15/113* (2013.01); *C12N 15/1135* (2013.01); *C12N 15/1137* (2013.01); *C12Q 1/02* (2013.01); *G01N 33/582* (2013.01); *H05K 999/99* (2013.01); *A61K 31/713* (2013.01); *C12N 2310/14* (2013.01); *C12N 2310/322* (2013.01); *C12N 2310/344* (2013.01); *C12N 2310/3515* (2013.01); *C12N 2310/531* (2013.01); *C12N 2320/30* (2013.01); *C12N 2320/32* (2013.01); *C12N 2320/35* (2013.01); *C12N 2320/53* (2013.01)

(58) Field of Classification Search
None
See application file for complete search history.

(56) References Cited

U.S. PATENT DOCUMENTS

| | | |
|---|---|---|
| 5,968,737 A | 10/1999 | Ali-Osman |
| 8,067,390 B2 | 11/2011 | Merritt |
| 8,367,628 B2 | 2/2013 | Goodwin |
| 8,664,376 B2 | 3/2014 | Niitsu |
| 8,686,052 B2 | 4/2014 | Niitsu |
| 8,710,209 B2 | 4/2014 | Jin |
| 8,741,867 B2 | 6/2014 | Niitsu |
| 8,895,717 B2 | 11/2014 | Sood |
| 9,151,758 B2 | 10/2015 | Zetter |
| 9,206,424 B2 | 12/2015 | Jin |
| 2004/0219600 A1 | 11/2004 | Williams |
| 2005/0255487 A1 | 11/2005 | Khvorova |
| 2007/0083334 A1 | 4/2007 | Mintz |
| 2007/0083945 A1 | 4/2007 | Byrum |
| 2013/0028885 A1 | 1/2013 | Zetter |
| 2013/0052160 A1 | 2/2013 | Zitvogel |
| 2013/0053270 A1 | 2/2013 | Gill |
| 2014/0134158 A1 | 5/2014 | Bardelli |
| 2014/0303237 A1 | 10/2014 | Shapiro et al. |
| 2014/0315975 A1 | 10/2014 | Niitsu |
| 2014/0315976 A1 | 10/2014 | Brahmbhatt et al. |
| 2016/0187319 A1 | 6/2016 | Tanaka |

FOREIGN PATENT DOCUMENTS

| | | |
|---|---|---|
| EP | 2724729 A1 | 4/2014 |
| WO | 1998021359 A1 | 5/1998 |
| WO | 2004094636 A1 | 11/2004 |
| WO | 2007061922 A2 | 5/2007 |
| WO | 2012176282 A1 | 12/2012 |
| WO | 2013192364 A1 | 12/2013 |
| WO | 2014098210 A1 | 6/2014 |

OTHER PUBLICATIONS

AC114115, GenBank Accession No. AC114115, Rattus norvegicus clone CH230-2808, Working Draft Sequence, 6 unordered pieces, May 13, 2003 [online]. [Retrieved on Apr. 30, 2016]. Retrieved from the internet <URL: http://www.ncbi.nlm.nih.gov/nuccore/AC114115>.

JU528663, GenBank Accession No. JU528663, TSA: Ctenomys sociabilis 330326.Ctso mRNA sequence, Oct. 10, 2012 [online]. [Retrieved on Apr. 30, 2016]. Retrieved from the internet <URL: http://www.ncbi.nlm.nih.gov/nuccore/JU528663>.

(Continued)

*Primary Examiner* — Richard A Schnizer
(74) *Attorney, Agent, or Firm* — Eckman Law Group

(57) ABSTRACT

This invention provides compounds, compositions and methods for modulating the expression of human GST-π using RNA interference. The RNA interference molecules can be used in methods for preventing or treating diseases such as malignant tumor. Provided are a range of siRNA structures, having one or more of nucleotides being modified or chemically-modified. Advantageous structures include siRNAs with 2'-deoxy nucleotides located in the seed region, as well as other nucleotide modifications.

23 Claims, 14 Drawing Sheets

(56) References Cited

OTHER PUBLICATIONS

GO761423, GenBank Accession No. G0761423, 0010260TNA004657HT OTNA Ovis aries cDNA 5-, mRNA sequence, May 8, 2009 [online]. [Retrieved on Apr. 30, 2016]. Retrieved from the internet <URL: http://www.ncbi.nlm.nih.gov/nucest/G0761423>.
GO786145, GenBank Accession No. G0786145, 0009200TNA002813HT OTNA Ovis aries cDNA 5-,.mRNA sequence, May 8, 2009 [online). [Retrieved on Apr. 30, 2016]. Retrieved from the internet <URL: http://www.ncbi.nlm.nih.gov/nucest/G0786145>.
AC230665, GenBank Accession No. AC230665, Bos taurus clone CH240-502B15, Jul. 10, 2008 [online]. [Retrieved on May 1, 2016]. Retrieved from the internet <URL:http://www.ncbi.nlm.nih.gov/nuccore/AC230665>.
AC230574, GenBank Accession No. AC230574, Bos taurus clone CH240-504M17, Jul. 10, 2008 [online]. [Retrieved on May 1, 2016]. Retrieved from the internet <URL:http://www.ncbi.nlm.nih.gov/nuccore/AC230574>.
BV207757, GenBank Accession No. BV207757, sqnm2244B3 Human DNA (Sequenom) *Homo sapiens* STS genomic, Oct. 17, 2009 [online]. [Retrieved on May 1, 2016]. Retrieved from the internet <URL: http://www.ncbi.nlm.nih.gov/nuccore/BV207757>.
AW374759, GenBank Accession No. AW374759, MR1-CT005B-291199-003-a05 CT0058 *Homo sapiens* cDNA. mRNA sequence, Jan. 9, 2011 [online]. (Retrieved on May 1, 2016). Retrieved from the internet <URL: http://www.ncbi.nlm.nih.gov/nucest/6B79413/>.
Love, Lipid-like materials for low-dose, in vivo gene silencing, Proc Natl Acad Sci U S A., 2010, vol. 107(5), pp. 1864-1869.
Xue, Small RNA combination therapy for lung cancer, Proc Natl Acad Sci U S A, 2014, vol. 111(34), pp. E3553-E3561.
Xu, Enhancing tumor cell response to chemotherapy through nanoparticle-mediated codelivery of siRNA and cisplatin prodrug, Proc Natl Acad Sci U S A, 2013, vol. 110, No. 46, pp. 18638-18643.
Ui-Tei, Functional dissection of siRNA sequence by systematic DNA substitution: modified siRNA with a DNA seed arm is a powerful tool for mammalian gene silencing with significantly reduced off-target effect, Nucleic Acids Res., 2008, vol. 36(7), pp. 2136-2151.
Niitsu, Serum Glutathione-S-Transferase-rr as a Tumor Marker for Gastrointestinal Malignancies, Cancer, Jan. 15, 1989, vol. 63, pp. 317-323.
Hirata, Significance of Glutathione S-Transferase-Pi as a Tumor Marker in Patients with Oral Cancer, Cancer, Nov. 15, 1992, vol. 70, No. 10, pp. 2381-2387.
Hida, Serum Glutathione S-Transferase-Pi Level as a Tumor Marker for Non-Small Cell Lung Cancer, Cancer, Mar. 1, 1994, vol. 73, No. 5, pp. 1377-1382.
Ban, Transfection of Glutathione S-Transferase (GST)-Pi Antisense Complementary DNA Increases the Sensitivity of a Colon Cancer Cell Line to Adriamycin, Cisplatin, Melphalan, and Etoposide, Cancer Research, Aug. 1, 1996, vol. 56, 3577-3582.
Morgan, Tumor Efficacy and Bone Marrow-sparing Properties of TER286, a Cytotoxin Activated by Glutathione S-Transferase, Cancer Research, Jun. 15. 1998, vol. 58, pp. 2568-2575.
Niitsu, A proof of glutathione S-transferase-pi-related multidrug resistance by transfer of antisense gene to cancer cells and sense gene to bone marrow stem cell, Chemico-Biological Interactions, 1998, vol. 111-112, pp. 325-332.
Miyanishi, Glutathione S-Transferase-pi Overexpression is Closely Associated With K-ras Mutation During Human Colon Carcinogenesis, Gastroenterology, 2001, vol. 121, pp. 865-874.
Matsunaga, C(H)OP refractory chronic lymphocytic leukemia patients in whom salvage chemotherapy chosen by evaluating multiple chemotherapeutic drug-resistant factors was remarkably effective, Int J Clin Oncol, 2003, vol. 8, pp. 326-331.
Hayashi, Suppressive effect of sulindac on branch duct-intraductal papillary mucinous neoplasms, J Gastroenterol, 2009, vol. 44, pp. 964-975.
Morse, The role of glutathione S-transferase P1-1 in colorectal cancer: friend or foe?, Gastroenterology, 2001, vol. 121(4), pp. 1010-1013.
Steckel, Determination of synthetic lethal interactions in KRAS oncogene-dependent cancer cells reveals novel therapeutic targeting strategies, Cell Res., 2012, vol. 22(8), pp. 1227-1245.
Collins, KRAS as a key oncogene and therapeutic target in pancreatic cancer, Front Physiol., 2013, vol. 4, Article 407, pp. 1-8.
Wagner, In Situ Evidence of KRAS Amplification and Association With Increased p21 Levels in Non-Small Cell Lung Carcinoma, 2009, Am J Clin Pathol, vol. 132, pp. 500-505.
https://cansar.icr.ac.uk/cansar/cell-lines/A549/mutations/ retrieved from the web on Jun. 20, 2016.
Valtorta, KRAS gene amplification in colorectal cancer and impact on response to EGFR-targeted therapy, 2013, Int. J. Cancer, vol. 133, pp. 1259-1266.
Birkeland, KRAS gene amplification and overexpression but not mutation associates with aggressive and metastatic endometrial cancer, 2012, British Journal of Cancer, vol. 107, pp. 1997-2004.
Ruan, Analysis of EGFR signaling pathway in nasopharyngeal carcinoma cells by quantitative phosphoproteomics, Proteome Science, Jun. 28, 2011, vol. 9, pp. 1-11.
Singhal, 1,3-Bis(3,5-dichlorophenyl) urea compound 'COH-SR4' inhibits proliferation and activates apoptosis in melanoma, Biochemical Pharmacology, Dec. 1, 2012, vol. 84, Iss. 11, pp. 1419-1427.
Hokaiwado, Glutathione S-transferase Pi mediates proliferation of androgen-independent prostate cancer cells, Carcinogenesis, Apr. 15, 2008, vol. 29, pp. 1134-1138.
Futreal, A Census of Human Cancer Genes, Nature Reviews Cancer 2004, vol. 4, pp. 177-183.
Takahashi et al., Gan To Kagaku Ryoho. 1994; 21 (7): 945-51, English summary p. 951.
Ban et al., Cancer Res. 1996; 56 (15): 3577-82, Transfection of Glutathione S-Transferase (GST)-n' Antisense complementary DNA Increases the Sensitivity of a Colon Cancer Cell Line to Adriamycin, Cisplatin, Melphalan, and Etoposide.
Nakajima et al., J Pharmacol Exp Ther. 2003; 306 (3): 861-9, Reversal of Multiple Drug Resistance in Cholangiocarcinoma by the Glutathione S-Transferase-Pi-Specific Inhibitor O1-Hexadecyl-gamma-glutamyl-S-benzylcysteinyl-D-phenylglycine Ethylester.
Hokaiwado et al., Carcinogenesis. 2008; 29 (6): 1134-8, Glutathione S-transferase Pi mediates proliferation of androgen-independent prostate cancer cells.
Adler et.al, EMBO J. 1999, 18, 1321-1334, Regulation of JNK signaling by GSTp.
Townsend, et. al, J. Biol. Chem. 2009, 284, 436-445, Novel Role for Glutathione S-Transferase Pi Regulator of Protein S-Glutathionylation Following Oxidative and Nitrosative Stress.
Yin et.al, Cancer Res. 2000 60, 4053-4057, Glutathione S-Transferase p Elicits Protection against H2O2-induced Cell Death via Coordinated Regulation of Stress Kinases.
Nishita et al., AACR 102nd Annual Meeting, Abstract No. 1065, 2011, Regulation of autophagy and MAPK signaling by glutathione S-transferase Pi in KRAS mutated cancer cells.
Jackson, Expression profiling reveals off-target gene regulation by RNAi, 2003, Nature Biotechnology, vol. 21, pp. 635-637.
Muller, Thiazolides inhibit growth and induce glutathione-S-transferase Pi (GSTP1)-dependent cell death in human colon cancer cells, 2008, Int. J. Cancer, vol. 123, pp. 1797-1806.
Sawers, Glutathione S-transferase Pi (GSTP1) directly influences platinum drug chemosensitivity in ovarian tumour cell lines, British Journal of Cancer, 2014, vol. 111, pp. 1150-1158.

RNA INTERFERENCE AGENTS FOR GST-PI GENE MODULATION

SEQUENCE LISTING

This application includes a Sequence Listing submitted electronically as an ASCII file created on Jan. 2, 2016, named ND5123385US_SL.txt, which is 112,822 bytes in size, and is hereby incorporated by reference in its entirety.

BACKGROUND OF THE INVENTION

Various human cancer tissues have been found to correlate with the appearance of mutated KRAS gene. In some cases, the tissues also present an elevated level of Glutathione S-Tranferase Pi (GST-π) expression. (Miyanishi et al., Gastroenterology, 2001, Vol. 121:865-874, Abstract) For example, elevated serum GST-π levels were observed in patients with various gastrointestinal malignancies. (Niitsu et al., Cancer, 1989, Vol. 63, No. 2, pp. 317-323, Abstract)

GST-π is a member of a GST family of enzymes that play a role in detoxification by catalyzing the conjugation of hydrophobic and electrophilic compounds with reduced glutathione. GST-π expression can be reduced in vitro with a siRNA. (Niitsu et al., US 2014/0315975 A1). However, there are many drawbacks of existing siRNA agents, such as insufficient activity, off target effects, lack of serum stability, and lack of in vivo potency or efficacy.

There is an urgent need for compositions and methods for modulating the expression of genes associated with cancer. In particular, therapeutics based on inhibition of GST-π expression will require highly potent and stable siRNA sequences and structures, which can reduce off target effects.

What is needed are siRNA sequences, compounds and structures for modulating GST-π expression, with uses for treating disease, such as malignant tumors.

BRIEF SUMMARY

This invention relates to the fields of biopharmaceuticals and therapeutics composed of nucleic acid based molecules. More particularly, this invention relates to compounds and compositions utilizing RNA interference (RNAi) for modulating the expression of human GST-π, and uses thereof.

This invention relates to compounds, compositions and methods for modulating the expression of human GST-π using RNA interference.

In some embodiments, this invention provides molecules for RNA interference gene silencing of GST-π.

In further embodiments, the structures, molecules and compositions of this invention can be used in methods for preventing or treating diseases, or ameliorating symptoms of conditions or disorders associated with GST-π, including malignant tumor.

Embodiments of this invention include the following:

A nucleic acid molecule for inhibiting expression of GST-π comprising a sense strand and an antisense strand, wherein the strands form a duplex region. The nucleic acid molecules can be siRNA molecules for inhibiting expression of GST-π, and may contain one or more nucleotides that are modified or chemically-modified.

In some embodiments, the nucleic acid siRNA molecules for inhibiting expression of GST-π may include 2'-deoxy nucleotides, 2'-O-alkyl substituted nucleotides, 2'-deoxy-2'-fluoro substituted nucleotides, or any combination thereof. In certain embodiments, the 2'-deoxy nucleotides may be in the seed region of the siRNA molecules. In certain aspects, the siRNA molecules for inhibiting expression of GST-π may have deoxynucleotides in a plurality of positions in the antisense strand.

The nucleic acid molecules of this invention may advantageously inhibit expression of GST-π mRNA with an IC50 of less than 300 pM. In certain embodiments, the nucleic acid molecules may inhibit expression of GST-π mRNA levels by at least 25% in vivo, upon a single administration of the molecules. In some embodiments, the nucleic acid molecules may have passenger strand off target activity reduced, or reduced by at least 50-fold, or at least 100-fold.

Embodiments of this invention further provide pharmaceutical compositions containing the siRNA molecules and a pharmaceutically acceptable carrier. In some embodiments, the carrier may be a lipid molecule, or liposome. This invention includes vectors or cells comprising the nucleic acid molecules.

Also contemplated in this invention are methods for treating a disease associated with GST-π expression, by administering to a subject in need a composition containing an siRNA, where the disease is malignant tumor, cancer, cancer caused by cells expressing mutated KRAS, sarcoma, or carcinoma.

BRIEF DESCRIPTION OF THE DRAWINGS

As shown in FIG. 1, after 43 days, the GST-π siRNA showed markedly advantageous tumor inhibition, with final primary tumor average weights significantly reduced by 2.8-fold, as compared to control.

In FIG. 4, the expression of PUMA was greatly increased from 2-6 days after transfection of the GST-π siRNA.

As shown in FIG. 5, at a dose of 4 mg/kg, significant reduction of about 40% in GST-π mRNA was detected 24 hours after injection.

As shown in FIG. 6, a dose response was obtained with doses ranging from 0.375 mg/kg to 3 mg/kg of siRNA targeted to GST-π. The GST-π siRNA showed advantageous tumor inhibition within a few days after administration, the tumor volume being reduced by about 2-fold at the endpoint.

As shown in FIG. 7, the half-life ($t_{1/2}$) in serum for both the sense strand (FIG. 7, top) and antisense strand (FIG. 7, bottom) of a GST-π siRNA was about 100 minutes.

FIG. 8 shows incubation of a liposomal formulation of a GST-π siRNA in 50% human serum in PBS, and detection of remaining siRNA at various time points. As shown in FIG. 8, the half-life ($t_{1/2}$) in plasma of the formulation of the GST-π siRNA was significantly longer than 100 hours.

As shown in FIG. 9, the guide strand knockdown of the GST-π siRNA was approximately exponential, as compared to a control with scrambled sequence that exhibited no effect.

As shown in FIG. 10, the passenger strand off target knockdown for the GST-π siRNA was greatly reduced, with essentially no effect.

As shown in FIG. 11, the guide strand knockdown activities of the GST-π siRNAs were approximately exponential.

As shown in FIG. 12, the passenger strand off target knockdown activities for the GST-π siRNAs were significantly reduced below about 500 pM.

As shown in FIG. 13, the guide strand knockdown activity of the GST-π siRNA was approximately exponential.

As shown in FIG. 14, the passenger strand off target knockdown activity for the GST-π siRNA was significantly reduced.

DETAILED DESCRIPTION OF THE INVENTION

Figure 1:
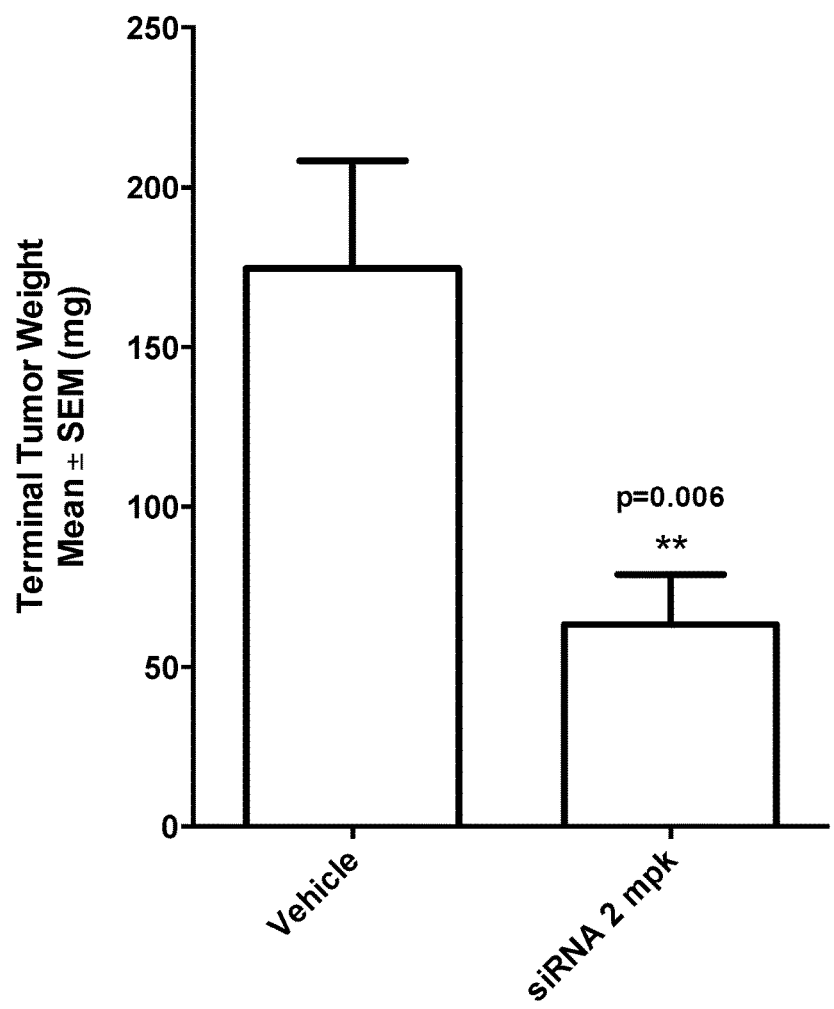
FIG. 1 shows the profound reduction of orthotopic lung cancer tumors in vivo by a siRNA of this invention targeted to GST-π. The GST-π siRNA was administered in a liposomal formulation at a dose of 2 mg/kg to athymic nude mice presenting A549 orthotopic lung cancer tumors. Final primary tumor weights were measured at necropsy for the treatment group and a vehicle control group. The GST-π siRNA showed significant efficacy for inhibition of lung cancer tumors in this six-week study.

This invention relates to compounds, compositions and methods for nucleic acid based therapeutics for modulating expression of GST-π.

In some embodiments, this invention provides molecules active in RNA interference, as well as structures and compositions that can silence expression of GST-π.

The structures and compositions of this disclosure can be used in preventing or treating various diseases such as malignant tumor.

In further embodiments, this invention provides compositions for delivery and uptake of one or more therapeutic RNAi molecules of this invention, as well as methods of use thereof. The RNA-based compositions of this invention can be used in methods for preventing or treating malignant tumors, such as cancers.

Therapeutic compositions of this invention include nucleic acid molecules that are active in RNA interference. The therapeutic nucleic acid molecules can be targeted to GSTP1 (GST-π) for gene silencing.

In various embodiments, this invention provides a range of molecules that can be active as a small interfering RNA (siRNA), and can regulate or silence GST-π gene expression.

The siRNAs of this invention can be used for preventing or treating malignant tumors.

Embodiments of this invention further provide a vehicle, formulation, or lipid nanoparticle formulation for delivery of the inventive siRNAs to subjects in need of preventing or treating a malignant tumor. This invention further contemplates methods for administering siRNAs as therapeutics to mammals.

The therapeutic molecules and compositions of this invention can be used for RNA interference directed to preventing or treating a GST-π associated disease, by administering a compound or composition to a subject in need.

The methods of this invention can utilize the inventive compounds for preventing or treating malignant tumor.

In some aspects, the malignant tumor can be presented in various diseases, for example, cancers that highly expressing GST-π, cancers caused by cells expressing mutated KRAS, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, and carcinomas.

In certain aspects, methods of this invention can utilize the inventive compounds for preventing or treating malignant tumors and cancers in any organ or tissue, including, for example, brain tumor, head and neck cancer, breast cancer, lung cancer, esophageal cancer, stomach cancer, duodenal cancer, colorectal cancer, liver cancer, pancreatic cancer, gallbladder cancer, bile duct cancer, kidney cancer, urethral cancer, bladder cancer, prostate cancer, testicular cancer, uterine cancer, ovary cancer, skin cancer, leukemia, malignant lymphoma, epithelial malignant tumors, and non-epithelial malignant tumors.

In certain embodiments, a combination of therapeutic molecules of this invention can be used for silencing or inhibiting GST-π gene expression.

This invention provides a range of RNAi molecules, where each molecule has a polynucleotide sense strand and a polynucleotide antisense strand; each strand of the molecule is from 15 to 30 nucleotides in length; a contiguous region of from 15 to 30 nucleotides of the antisense strand is complementary to a sequence of an mRNA encoding GST-π; and at least a portion of the sense strand is complementary to at least a portion of the antisense strand, and the molecule has a duplex region of from 15 to 30 nucleotides in length.

A RNAi molecule of this invention can have a contiguous region of from 15 to 30 nucleotides of the antisense strand that is complementary to a sequence of an mRNA encoding GST-π, which is located in the duplex region of the molecule.

In some embodiments, a RNAi molecule can have a contiguous region of from 15 to 30 nucleotides of the antisense strand that is complementary to a sequence of an mRNA encoding GST-π.

Embodiments of this invention may further provide methods for preventing, treating or ameliorating one or more symptoms of malignant tumor, or reducing the risk of developing malignant tumor, or delaying the onset of malignant tumor in a mammal in need thereof.

GST-π and RNAi Molecules

The nucleic acid sequence of an example target human glutathione S-transferase pi (human GST-π) mRNA is disclosed in GenBank accession number NM_000852.3 (hG-STP1), and is 986 nucleotides in length.

One of ordinary skill in the art would understand that a reported sequence may change over time and to incorporate any changes needed in the nucleic acid molecules herein accordingly.

Embodiments of this invention can provide compositions and methods for gene silencing of GST-π expression using small nucleic acid molecules. Examples of nucleic acid molecules include molecules active in RNA interference (RNAi molecules), short interfering RNA (siRNA), double-stranded RNA (dsRNA), micro-RNA (miRNA), and short hairpin RNA (shRNA) molecules, as well as DNA-directed RNAs (ddRNA), Piwi-interacting RNAs (piRNA), and repeat associated siRNAs (rasiRNA). Such molecules are capable of mediating RNA interference against GST-π gene expression.

The composition and methods disclosed herein can also be used in treating various kinds of malignant tumors in a subject.

The nucleic acid molecules and methods of this invention may be used to down regulate the expression of genes that encode GST-π.

The compositions and methods of this invention can include one or more nucleic acid molecules, which, independently or in combination, can modulate or regulate the expression of GST-π protein and/or genes encoding GST-π proteins, proteins and/or genes encoding GST-π associated with the maintenance and/or development of diseases, conditions or disorders associated with GST-π, such as malignant tumor.

The compositions and methods of this invention are described with reference to exemplary sequences of GST-π. A person of ordinary skill in the art would understand that various aspects and embodiments of the invention are directed to any related GST-π genes, sequences, or variants, such as homolog genes and transcript variants, and polymorphisms, including single nucleotide polymorphism (SNP) associated with any GST-π genes.

In some embodiments, the compositions and methods of this invention can provide a double-stranded short interfering nucleic acid (siRNA) molecule that downregulates the expression of a GST-π gene, for example human GST-π.

A RNAi molecule of this invention can be targeted to GST-π and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing GST-π targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of this invention include RNAi molecules that are active against GST-π mRNA, where the RNAi molecule includes a sequence complementary to any mRNA encoding a GST-π sequence.

In some embodiments, a RNAi molecule of this disclosure can have activity against GST-π RNA, where the RNAi molecule includes a sequence complementary to an RNA having a variant GST-π encoding sequence, for example, a mutant GST-π gene known in the art to be associated with malignant tumor.

In further embodiments, a RNAi molecule of this invention can include a nucleotide sequence that can interact with a nucleotide sequence of a GST-π gene and mediate silencing of GST-π gene expression.

The nucleic acid molecules for inhibiting expression of GST-π may have a sense strand and an antisense strand, wherein the strands form a duplex region. The nucleic acid molecules may have one or more of the nucleotides in the duplex region being modified or chemically-modified, including such modifications as are known in the art. Any nucleotide in an overhang of the siRNA may also be modified or chemically-modified.

In some embodiments, the preferred modified or chemically-modified nucleotides are 2'-deoxy nucleotides. In additional embodiments, the modified or chemically-modified nucleotides can include 2'-O-alkyl substituted nucleotides, 2'-deoxy-2'-fluoro substituted nucleotides, phosphorothioate nucleotides, locked nucleotides, or any combination thereof.

In certain embodiments, a preferred structure can have an antisense strand containing deoxynucleotides in a plurality of positions, the plurality of positions being one of the following: each of positions 4, 6 and 8, from the 5' end of the antisense strand; each of positions 3, 5 and 7, from the 5' end of the antisense strand; each of positions 1, 3, 5 and 7, from the 5' end of the antisense strand; each of positions 3-8, from the 5' end of the antisense strand; and each of positions 5-8, from the 5' end of the antisense strand. Any of these structures can be combined with one or more 2'-deoxy-2'-fluoro substituted nucleotides in the duplex region.

The nucleic acid molecules of this invention can inhibit expression of GST-π mRNA with an advantageous IC50 of less than about 300 pM, or less than about 200 pM, or less than about 100 pM, or less than about 50 pM.

Further, the nucleic acid molecules can inhibit expression of GST-π mRNA levels by at least 25% in vivo, upon a single administration.

Pharmaceutical compositions are contemplated in this invention, which can contain one or more siRNAs as described herein, in combination with a pharmaceutically acceptable carrier. Any suitable carrier may be used, including those known in the art, as well as lipid molecules, nanoparticles, or liposomes, any of which may encapsulate the siRNA molecules.

This invention discloses methods for treating a disease associated with GST-π expression, which methods include administering to a subject in need a composition containing one or more of the siRNAs. Diseases to be treated may include malignant tumor, cancer, cancer caused by cells expressing mutated KRAS, sarcoma, and carcinoma, among others.

Examples of RNAi molecules of this invention targeted to GST-π mRNA are shown in Table 1.

TABLE 1

RNAi molecule sequences for GST-π

| ID | Ref Pos | SEQ ID NO | SENSE STRAND (5'→3') SEQ ID NOS: 1 to 65 | SEQ ID NO | ANTISENSE STRAND (5'→3') SEQ ID NOS: 66 to 130 |
|---|---|---|---|---|---|
| A1 | 652 | 1 | UCCCAGAACCAGGGAGGCAtt | 66 | UGCCUCCCUGGUUCUGGGAca |
| A10 | 635 | 2 | CUUUUGAGACCCUGCUGUCtt | 67 | GACAGCAGGGUCUCAAAAGgc |
| A11 | 649 | 3 | CUGUCCCAGAACCAGGGAGtt | 68 | CUCCCUGGUUCUGGGACAGca |
| A12 | 650 | 4 | UGUCCCAGAACCAGGGAGGtt | 69 | CCUCCCUGGUUCUGGGACAgc |
| A13 | 631 | 5 | AAGCCUUUUGAGACCCUGCtt | 70 | GCAGGGUCUCAAAAGGCUUca |
| A14 | 638 | 6 | UUGAGACCCUGCUGUCCCAtt | 71 | UGGGACAGCAGGGUCUCAAaa |
| A15 | 636 | 7 | UUUUGAGACCCUGCUGUCCtt | 72 | GGACAGCAGGGUCUCAAAAgg |
| A16 | 640 | 8 | GAGACCCUGCUGUCCCAGAtt | 73 | UCUGGGACAGCAGGGUCUCaa |
| A17 | 332 | 9 | GCUGGAAGGAGGAGGUGGUtt | 74 | ACCACCUCCUCCUUCCAGCtc |
| A18 | 333 | 10 | CUGGAAGGAGGAGGUGGUGtt | 75 | CACCACCUCCUCCUUCCAGct |
| A19 | 321 | 11 | UCAGGGCCAGAGCUGGAAGtt | 76 | CUUCCAGCUCUGGCCCUGAtc |
| A2 | 639 | 12 | UGAGACCCUGCUGUCCCAGtt | 77 | CUGGGACAGCAGGGUCUCAaa |
| A20 | 323 | 13 | AGGGCCAGAGCUGGAAGGAtt | 78 | UCCUUCCAGCUCUGGCCCUga |
| A21 | 331 | 14 | AGCUGGAAGGAGGAGGUGGtt | 79 | CCACCUCCUCCUUCCAGCUct |
| A22 | 641 | 15 | AGACCCUGCUGUCCCAGAAtt | 80 | UUCUGGGACAGCAGGGUCUca |
| A23 | 330 | 16 | GAGCUGGAAGGAGGAGGUGtt | 81 | CACCUCCUCCUUCCAGCUCtg |
| A25 | 647 | 17 | UGCUGUCCCAGAACCAGGGtt | 82 | CCCUGGUUCUGGGACAGCAgg |
| A26 | 653 | 18 | CCCAGAACCAGGGAGGCAAtt | 83 | UUGCCUCCCUGGUUCUGGGac |
| A3 | 654 | 19 | CCAGAACCAGGGAGGCAAGtt | 84 | CUUGCCUCCCUGGUUCUGGga |
| A4 | 637 | 20 | UUUGAGACCCUGCUGUCCCtt | 85 | GGGACAGCAGGGUCUCAAAag |
| AS | 642 | 21 | GACCCUGCUGUCCCAGAACtt | 86 | GUUCUGGGACAGCAGGGUCtc |
| A6 | 319 | 22 | GAUCAGGGCCAGAGCUGGAtt | 87 | UCCAGCUCUGGCCCUGAUCtg |
| A7 | 632 | 23 | AGCCUUUUGAGACCCUGCUtt | 88 | AGCAGGGUCUCAAAAGGCUtc |
| A8 | 633 | 24 | GCCUUUUGAGACCCUGCUGtt | 89 | CAGCAGGGUCUCAAAAGGCtt |
| A9 | 634 | 25 | CCUUUUGAGACCCUGCUGUtt | 90 | ACAGCAGGGUCUCAAAAGGct |
| AG7 | 632 | 26 | CGCCUUUUGAGACCCUGCAtt | 91 | UGCAGGGUCUCAAAAGGCGtc |
| AK1 | 257 | 27 | CCUACACCGUGGUCUAUUUtt | 92 | AAAUAGACCACGGUGUAGGgc |
| AK10 | 681 | 28 | UGUGGGAGACCAGAUCUCCtt | 93 | GGAGAUCUGGUCUCCCACAat |
| AK11 | 901 | 29 | GCGGGAGGCAGAGUUUGCCtt | 94 | GGCAAACUCUGCCUCCCGCtc |
| AK12 | 922 | 30 | CCUUUCUCCAGGACCAAUAtt | 95 | UAUUGGUCCUGGAGAAAGGaa |
| AK13/A24 | 643 | 31 | ACCCUGCUGUCCCAGAACCtt | 96 | GGUUCUGGGACAGCAGGGUct |
| AK2 | 267 | 32 | GGUCUAUUUCCCAGUUCGAtt | 97 | UCGAACUGGGAAAUAGACCac |
| AK3 | 512 | 33 | CCCUGGUGGACAUGGUGAAtt | 98 | UUCACCAUGUCCACCAGGGct |
| AK4 | 560 | 34 | ACAUCUCCCUCAUCUACACtt | 99 | GUGUAGAUGAGGGAGAUGUat |
| AK5 | 593 | 35 | GCAAGGAUGACUAUGUGAAtt | 100 | UUCACAUAGUCAUCCUUGCcc |
| AK6 | 698 | 36 | CCUUCGCUGACUACAACCUtt | 101 | AGGUUGUAGUCAGCGAAGGag |

TABLE 1-continued

| | | | SENSE STRAND (5'→3') | | ANTISENSE STRAND (5'→3') |
|---|---|---|---|---|---|
| ID | Ref Pos | SEQ ID NO | SEQ ID NOS: 1 to 65 | SEQ ID NO | SEQ ID NOS: 66 to 130 |
| AK7 | 313 | 37 | CUGGCAGAUCAGGGCCAGAtt | 102 | UCUGGCCCUGAUCUGCCAGca |
| AK8 | 421 | 38 | GACGGAGACCUCACCCUGUtt | 103 | ACAGGGUGAGGUCUCCGUCct |
| AK9 | 590 | 39 | CGGGCAAGGAUGACUAUGUtt | 104 | ACAUAGUCAUCCUUGCCCGcc |
| AU10 | 635 | 40 | CUUUUGAGACCCUGCUGUAtt | 105 | UACAGCAGGGUCUCAAAAGgc |
| AU23 | 330 | 41 | GAGCUGGAAGGAGGAGGUAtt | 106 | UACCUCCUCCUUCCAGCUCtg |
| AU24 | 643 | 42 | ACCCUGCUGUCCCAGAACAtt | 107 | UGUUCUGGGACAGCAGGGUct |
| AU25 | 648 | 43 | UGCUGUCCCAGAACCAGGAtt | 108 | UCCUGGUUCUGGGACAGCAgg |
| AU7 | 632 | 44 | AGCCUUUUGAGACCCUGCAtt | 109 | UGCAGGGUCUCAAAAGGCUtc |
| AU9 | 634 | 45 | CCUUUUGAGACCCUGCUGAtt | 110 | UCAGCAGGGUCUCAAAAGGct |
| B1 | 629 | 46 | UGAAGCCUUUUGAGACCCUtt | 111 | AGGGUCUCAAAAGGCUUCAgt |
| B10 | 627 | 47 | ACUGAAGCCUUUUGAGACCtt | 112 | GGUCUCAAAAGGCUUCAGUtg |
| B11 | 596 | 48 | AGGAUGACUAUGUGAAGGCtt | 113 | GCCUUCACAUAGUCAUCCUtg |
| B12 | 597 | 49 | GGAUGACUAUGUGAAGGCAtt | 114 | UGCCUUCACAUAGUCAUCCtt |
| B13 | 598 | 50 | GAUGACUAUGUGAAGGCACtt | 115 | GUGCCUUCACAUAGUCAUCct |
| B14 | 564 | 51 | CUCCCUCAUCUACACCAACtt | 116 | GUUGGUGUAGAUGAGGGAGat |
| B2 | 630 | 52 | GAAGCCUUUUGAGACCCUGtt | 117 | CAGGGUCUCAAAAGGCUUCag |
| B3 | 563 | 53 | UCUCCCUCAUCUACACCAAtt | 118 | UUGGUGUAGAUGAGGGAGAtg |
| B4 | 567 | 54 | CCUCAUCUACACCAACUAUtt | 119 | AUAGUUGGUGUAGAUGAGGga |
| B5 | 566 | 55 | CCCUCAUCUACACCAACUAtt | 120 | UAGUUGGUGUAGAUGAGGGag |
| B6 | 625 | 56 | CAACUGAAGCCUUUUGAGAtt | 121 | UCUCAAAAGGCUUCAGUUGcc |
| B7 | 626 | 57 | AACUGAAGCCUUUUGAGACtt | 122 | GUCUCAAAAGGCUUCAGUUgc |
| B8 | 628 | 58 | CUGAAGCCUUUUGAGACCCtt | 123 | GGGUCUCAAAAGGCUUCAGtt |
| B9 | 565 | 59 | UCCCUCAUCUACACCAACUtt | 124 | AGUUGGUGUAGAUGAGGGAga |
| BG3 | 563 | 60 | GCUCCCUCAUCUACACCAAtt | 125 | UUGGUGUAGAUGAGGGAGCtg |
| BU2 | 630 | 61 | GAAGCCUUUUGAGACCCUAtt | 126 | UAGGGUCUCAAAAGGCUUCag |
| BU10 | 627 | 62 | ACUGAAGCCUUUUGAGACAtt | 127 | UGUCUCAAAAGGCUUCAGUtg |
| BU14 | 565 | 63 | CUCCCUCAUCUACACCAAAtt | 128 | UUUGGUGUAGAUGAGGGAGat |
| BU4 | 567 | 64 | CCUCAUCUACACCAACUAAtt | 129 | UUAGUUGGUGUAGAUGAGGga |
| C1-934 | 934 | 65 | ACCAAUAAAAUUUCUAAGAtt | 130 | UCUUAGAAAUUUUAUUGGUcc |

Key for Table 1: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine respectively.

Examples of RNAi molecules of this invention targeted to GST-π mRNA are shown in Table 2.

letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide. An "s" character represents a phosphorothioate linkage.

TABLE 2

RNAi molecule sequences for GST-π

| ID | SEQ ID NO | SENSE STRAND (5'→3') SEQ ID NOS: 131 to 156 | SEQ ID NO | ANTISENSE STRAND (5'→3') SEQ ID NOS: 157 to 182 |
|---|---|---|---|---|
| BU2' | 131 | GAAGCCUUUUGAGACCCUANN | 157 | UAGGGUCUCAAAAGGCUUCNN |
| 14 | 132 | GAAGCCUUUUGAGACCCUAUU | 158 | UAGGGUCUCAAAAGGCUUCUU |
| 15 | 133 | GAAGCCUUUUGAGACCCUAUU | 159 | uagggucuCAAAAGGCUUCUU |
| 16 | 134 | GAAGCCUUUUGAGACCCUAUU | 160 | UagggucuCAAAAGGCUUCUU |
| 17 | 135 | GAAGCCUUUUGAGACCCUAUU | 161 | UAgggucuCAAAAGGCUUCUU |
| 18 | 136 | GAAGCCUUUUGAGACCCUAUU | 162 | UAGggucuCAAAAGGCUUCUU |
| 19 | 137 | GAAGCCUUUUGAGACCCUAUU | 163 | UAGGgucuCAAAAGGCUUCUU |
| 20 | 138 | GAAGCCUUUUGAGACCCUAUU | 164 | uAgGgUcUCAAAAGGCUUCUU |
| 21 | 139 | GAAGCCUUUUGAGACCCUAUU | 165 | UAgGgUcUCAAAAGGCUUCUU |
| 22 | 140 | GAAGCCUUUUGAGACCCUAUU | 166 | UaGgGuCuCAAAAGGCUUCUU |
| 23 | 141 | GAAGCCUUUUGAGACCCUAUU | 167 | UAGgGuCuCAAAAGGCUUCUU |
| 24 | 142 | GAAGCCUUUUGAGACCCUAtt | 168 | UagggucuCAAAAGGCUUCUU |
| 25 | 143 | GAAGCCUUUUGAGACCCUAUU | 169 | UAGGGUCUCAAAAGGCUUCUU |
| 26 | 144 | GAAGCCUUUUGAGACCCUAUU | 170 | fUAGGGUCUCAAAAGGCUUCUU |
| 27 | 145 | GAAGCCUUUUGAGACCCUAUU | 171 | uAGGGUCUCAAAAGGCUUCUU |
| 28 | 146 | GAAGCCUUUUGAGACCCUAUU | 172 | UsAGGGUCUCAAAAGGCUUCUU |
| 29 | 147 | GAAGCCUUUUGAGACCCUfAUU | 173 | fUAGGGUCUfCAAAAGGCfUUCUU |
| 30 | 148 | GAAGCCUUUUGAGfACCCUfAUU | 174 | fUAGGGUCUfCAfAfAAGGCfUUCUU |
| 31 | 149 | GAAGCCUUUUGAGACCCUAUU | 175 | UAGGGUCUCAAAAGGCUUCUU |
| 31' | 150 | GAAGCCUUUUGAGACCCUAUU | 176 | fUAGGGUCUCAAAAGGCUUCUU |
| 32 | 151 | GAAGCCUUUUGAGACCCUAUU | 177 | UAGGGUCUCAAAAGGCUUCUU |
| 39 | 152 | GAAGCCUUUUGAGACCCUAUU | 178 | UAGgGuCuCAAAAGGCUUCUU |
| 45 | 153 | GAAGCCUUUUGAGACCCUAUU | 179 | UAGgGuCuCAAAAGGCUUCUU |
| 46 | 154 | GAAGCCUUUUGAGACCCUAUU | 180 | UAGgGuCuCAAAAGGCUUCUU |
| 47 | 155 | GAAGCCUUUUGAGACCCUAUU | 181 | UAGgGuCuCAAAAGGCUUCUU |
| 48 | 156 | GAAGCCUUUUGAGACCCUAUU | 182 | fUAGgGuCuCAAAAGGCUUCUU |

Key for Table 2: Upper case A, G, C and U refer to ribo-A, ribo-G, ribo-C and ribo-U, respectively. The lower case Examples of RNAi molecules of this invention targeted to GST-π mRNA are shown in Table 3.

TABLE 3

RNAi molecule sequences for GST-π

| ID | SEQ ID NO | SENSE STRAND (5'→3') SEQ ID NOS: 207 to 221 | SEQ ID NO | ANTISENSE STRAND (5'→3') SEQ ID NOS: 222 to 236 |
|---|---|---|---|---|
| A9' | 183 | CCUUUGAGACCCUGCUGUNN | 195 | ACAGCAGGGUCUCAAAAGGNN |
| 1 | 184 | CCUCAUCUACACCAACUAU<u>UU</u> | 196 | AUAGUUGGUGUAGAUGAGG<u>UU</u> |
| 2 | 185 | CCUCAUCUACACCAACUAU<u>UU</u> | 197 | auaguugg<u>UGUAGAUGAGGUU</u> |
| 3 | 186 | CCUCAUCUACACCAACUAU<u>UU</u> | 198 | Auaguugg<u>UGUAGAUGAGGUU</u> |
| 4 | 187 | CCUCAUCUACACCAACUAU<u>UU</u> | 199 | AUaguugg<u>UGUAGAUGAGGUU</u> |
| 5 | 188 | CCUCAUCUACACCAACUAU<u>UU</u> | 200 | AUAguugg<u>UGUAGAUGAGGUU</u> |
| 6 | 189 | CCUCAUCUACACCAACUAU<u>UU</u> | 201 | AUAGuugg<u>UGUAGAUGAGGUU</u> |
| 7 | 190 | CCUCAUCUACACCAACUAU<u>UU</u> | 202 | a<u>U</u>aG<u>U</u>g<u>U</u>g<u>GUGUAGAUGAGGUU</u> |
| 8 | 191 | CCUCAUCUACACCAACUAU<u>UU</u> | 203 | A<u>U</u>aG<u>U</u>g<u>GUGUAGAUGAGGUU</u> |
| 9 | 192 | CCUCAUCUACACCAACUAU<u>UU</u> | 204 | A<u>U</u>A<u>g</u>U<u>u</u>G<u>g</u>U<u>GUAGAUGAGGUU</u> |
| 10 | 193 | CCUCAUCUACACCAACUAU<u>UU</u> | 205 | A<u>U</u>A<u>g</u>U<u>u</u>G<u>g</u>U<u>GUAGAUGAGGUU</u> |
| 11 | 194 | <u>CCUCAUCUACACCAACUAUUU</u> | 206 | Auaguugg<u>UGUAGAUGAGGUU</u> |

Key for Table 3: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, <u>U</u>, a, c, g, u, t, or a modified, inverted, or chemically modified nucleotide.

Examples of RNAi molecules of this invention targeted to GST-π mRNA are shown in Table 4.

TABLE 4

RNAi molecule sequences for GST-π

| ID | SEQ ID NO | SENSE STRAND (5'→3') SEQ ID NOS: 207 to 221 | SEQ ID NO | ANTISENSE STRAND (5'→3') SEQ ID NOS: 222 to 236 |
|---|---|---|---|---|
| B13' | 207 | GAUGACUAUGUGAAGGCACNN | 222 | GUGCCUUCACAUAGUCAUCNN |
| 4 | 208 | GGAUGACUAUGUGAAGGCA<u>UU</u> | 223 | UGCCUUCACAUAGUCAUCC<u>UU</u> |
| 5 | 209 | GGAUGACUAUGUGAAGGCA<u>UU</u> | 224 | ugccuuca<u>CAUAGUCAUCCUU</u> |
| 6 | 210 | GGAUGACUAUGUGAAGGCA<u>UU</u> | 225 | Ugccuuca<u>CAUAGUCAUCCUU</u> |
| 7 | 211 | GGAUGACUAUGUGAAGGCA<u>UU</u> | 226 | UGccuuca<u>CAUAGUCAUCCUU</u> |
| 8 | 212 | GGAUGACUAUGUGAAGGCA<u>UU</u> | 227 | UGCcuuca<u>CAUAGUCAUCCUU</u> |
| 9 | 213 | GGAUGACUAUGUGAAGGCA<u>UU</u> | 228 | UGCCuuca<u>CAUAGUCAUCCUU</u> |
| 10 | 214 | GGAUGACUAUGUGAAGGCA<u>UU</u> | 229 | uGc<u>U</u>c<u>U</u>cACAUAGUCAUCC<u>UU</u> |
| 11 | 215 | GGAUGACUAUGUGAAGGCA<u>UU</u> | 230 | UGc<u>U</u>c<u>U</u>cACAUAGUCAUCC<u>UU</u> |
| 12 | 216 | GGAUGACUAUGUGAAGGCA<u>UU</u> | 231 | U<u>g</u>C<u>c</u>U<u>u</u>C<u>a</u>CAUAGUCAUCC<u>UU</u> |
| 13 | 217 | GGAUGACUAUGUGAAGGCA<u>UU</u> | 232 | UGC<u>c</u>U<u>u</u>C<u>a</u>CAUAGUCAUCC<u>UU</u> |
| 14 | 218 | <u>GGAUGA</u>C<u>U</u>AUGUGAAGGCA<u>UU</u> | 233 | Ugccuuca<u>CAUAGUCAUCCUU</u> |
| 15 | 219 | GGAUGACUAUfGUfGAAGGCA<u>UU</u> | 234 | UGCfCUUCACAUAGUCAUCC<u>UU</u> |
| 17 | 220 | <u>GGAUGACUAUGUGAAGGCAUU</u> | 235 | UGCCUUCA<u>CAUAGUCAUCCUU</u> |
| 18 | 221 | <u>GGAUGACUAUGUGAAGGCAUU</u> | 236 | UGCCUUCAC<u>AUAGUCAUCCUU</u> |

Key for Table 4: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 5.

TABLE 5

RNAi molecule sequences for GST-π

| ID | SEQ ID NO | SENSE STRAND (5'→3') SEQ ID NOS: 237 to 248 | SEQ ID NO | ANTISENSE STRAND (5'→3') SEQ ID NOS: 249 to 260 |
|---|---|---|---|---|
| B2' | 237 | GAAGCCUUUUGAGACCCUGNN | 249 | CAGGGUCUCAAAAGGCUUCNN |
| 1 | 238 | GAAGCCUUUUGAGACCCUGUU | 250 | CAGGGUCUCAAAAGGCUUCUU |
| 2 | 239 | GAAGCCUUUUGAGACCCUGUU | 251 | cagggucuCAAAAGGCUUCUU |
| 3 | 240 | GAAGCCUUUUGAGACCCUGUU | 252 | CagggucuCAAAAGGCUUCUU |
| 4 | 241 | GAAGCCUUUUGAGACCCUGUU | 253 | CAgggucuCAAAAGGCUUCUU |
| 5 | 242 | GAAGCCUUUUGAGACCCUGUU | 254 | CAGgucuCAAAAGGCUUCUU |
| 6 | 243 | GAAGCCUUUUGAGACCCUGUU | 255 | CAGGgucuCAAAAGGCUUCUU |
| 7 | 244 | GAAGCCUUUUGAGACCCUGUU | 256 | cAgGgUcUCAAAAGGCUUCUU |
| 8 | 245 | GAAGCCUUUUGAGACCCUGUU | 257 | CAgGgUcUCAAAAGGCUUCUU |
| 9 | 246 | GAAGCCUUUUGAGACCCUGUU | 258 | CaGgGuCuCAAAAGGCUUCUU |
| 10 | 247 | GAAGCCUUUUGAGACCCUGUU | 259 | CAGgGuCuCAAAAGGCUUCUU |
| 11 | 248 | GAAGCCUUUUGAGACCCUGUU | 260 | CagggucuCAAAAGGCUUCUU |

Key for Table 5: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 6.

TABLE 6

RNAi molecule sequences for GST-π

| ID | SEQ ID NO | SENSE STRAND (5'→3') SEQ ID NOS: 261 to 272 | SEQ ID NO | ANTISENSE STRAND (5'→3') SEQ ID NOS: 273 to 284 |
|---|---|---|---|---|
| B4' | 261 | CCUCAUCUACACCAACUAUNN | 273 | AUAGUUGGUGUAGAUGAGGNN |
| 1 | 262 | CCUCAUCUACACCAACUAUUU | 274 | AUAGUUGGUGUAGAUGAGGUU |
| 2 | 263 | CCUCAUCUACACCAACUAUUU | 275 | auaguuggUGUAGAUGAGGUU |
| 3 | 264 | CCUCAUCUACACCAACUAUUU | 276 | AuaguuggUGUAGAUGAGGUU |
| 4 | 265 | CCUCAUCUACACCAACUAUUU | 277 | AUaguuggUGUAGAUGAGGUU |
| 5 | 266 | CCUCAUCUACACCAACUAUUU | 278 | AUAguuggUGUAGAUGAGGUU |
| 6 | 267 | CCUCAUCUACACCAACUAUUU | 279 | AUAGuuggUGUAGAUGAGGUU |
| 7 | 268 | CCUCAUCUACACCAACUAUUU | 280 | aUaGuUgGUGUAGAUGAGGUU |
| 8 | 269 | CCUCAUCUACACCAACUAUUU | 281 | AUaGuUgGUGUAGAUGAGGUU |

TABLE 6-continued

RNAi molecule sequences for GST-π

| ID | SEQ ID NO | SENSE STRAND (5'→3') SEQ ID NOS: 261 to 272 | SEQ ID NO | ANTISENSE STRAND (5'→3') SEQ ID NOS: 273 to 284 |
|---|---|---|---|---|
| 9 | 270 | CCUCAUCUACACCAACUAU<u>UU</u> | 282 | AuAgUuGgUGUAGAUGAGG<u>UU</u> |
| 10 | 271 | CCUCAUCUACACCAACUA<u>UUU</u> | 283 | AUAgUuGgUGUAGAUGAGG<u>UU</u> |
| 11 | 272 | <u>CC</u>U<u>C</u>A<u>UC</u>U<u>A</u>CACCAACUAU<u>UU</u> | 284 | AuaguuggUGUAG<u>AUGA</u>GGUU |

Key for Table 6: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, <u>U</u>, a, c, g, u, t, or a modified, inverted, or chemically modified nucleotide.

In some embodiments, this invention provides a range of nucleic acid molecules, wherein: a) the molecule has a polynucleotide sense strand and a polynucleotide antisense strand; b) each strand of the molecule is from 15 to 30 nucleotides in length; c) a contiguous region of from 15 to 30 nucleotides of the antisense strand is complementary to a sequence of an mRNA encoding GST-π; d) at least a portion of the sense strand is complementary to at least a portion of the antisense strand, and the molecule has a duplex region of from 15 to 30 nucleotides in length.

In some embodiments, the nucleic acid molecule can have contiguous region of from 15 to 30 nucleotides of the antisense strand that is complementary to a sequence of an mRNA encoding GST-π is located in the duplex region of the molecule.

In additional embodiments, the nucleic acid molecule can have a contiguous region of from 15 to 30 nucleotides of the antisense strand that is complementary to a sequence of an mRNA encoding GST-π.

In certain embodiments, each strand of the nucleic acid molecule can be from 18 to 22 nucleotides in length. The duplex region of the nucleic acid molecule can be 19 nucleotides in length.

In alternative forms, the nucleic acid molecule can have a polynucleotide sense strand and a polynucleotide antisense strand that are connected as a single strand, and form a duplex region connected at one end by a loop.

Some embodiments of a nucleic acid molecule of this disclosure can have a blunt end. In certain embodiments, a nucleic acid molecule can have one or more 3' overhangs.

This invention provides a range of nucleic acid molecules that are RNAi molecules active for gene silencing. The inventive nucleic acid molecules can be a dsRNA, a siRNA, a micro-RNA, or a shRNA active for gene silencing, as well as a DNA-directed RNA (ddRNA), Piwi-interacting RNA (piRNA), or a repeat associated siRNA (rasiRNA). The nucleic acid molecules can be active for inhibiting expression of GST-π.

Embodiments of this invention further provide nucleic acid molecules having an IC50 for knockdown of GST-π of less than 100 pM.

Additional embodiments of this invention provide nucleic acid molecules having an IC50 for knockdown of GST-π of less than 50 pM.

This invention further contemplates compositions containing one or more of the inventive nucleic acid molecules, along with a pharmaceutically acceptable carrier. In certain embodiments, the carrier can be a lipid molecule or liposome.

The compounds and compositions of this invention are useful in methods for preventing or treating a GST-π associated disease, by administering a compound or composition to a subject in need.

The methods of this invention can utilize the inventive compounds for preventing or treating malignant tumor. The malignant tumor can be presented in various diseases, for example, cancers associated with GST-π expression, cancers caused by cells expressing mutated KRAS, sarcomas, fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, osteosarcoma, carcinomas, brain tumor, head and neck cancer, breast cancer, lung cancer, esophageal cancer, stomach cancer, duodenal cancer, appendix cancer, colorectal cancer, rectal cancer, liver cancer, pancreatic cancer, gallbladder cancer, bile duct cancer, anus cancer, kidney cancer, urethral cancer, urinary bladder cancer, prostate cancer, testicular cancer, uterine cancer, ovary cancer, skin cancer, leukemia, malignant lymphoma, epithelial malignant tumors, and non-epithelial malignant tumors.

Modified and Chemically-Modified siRNAs

Embodiments of this invention encompass siRNA molecules that are modified or chemically-modified to provide enhanced properties for therapeutic use, such as increased activity and potency for gene silencing. This invention provides modified or chemically-modified siRNA molecules that can have increased serum stability, as well as reduced off target effects, without loss of activity and potency of the siRNA molecules for gene modulation and gene silencing. In some aspects, this invention provides siRNAs having modifications or chemical modifications in various combinations, which enhance the stability and efficacy of the siRNA.

In some embodiments, the siRNA molecules of this invention can have passenger strand off target activity reduced by at least 10-fold, or at least 20-fold, or at least 30-fold, or at least 50-fold, or at least 100-fold.

As used herein, the terms modified and chemically-modified refer to changes made in the structure of a naturally-occurring nucleotide or nuclei acid structure of an siRNA, which encompasses siRNAs having one or more nucleotide analogs, altered nucleotides, non-standard nucleotides, non-naturally occurring nucleotides, and combinations thereof.

In some embodiments, the number of modified or chemically-modified structures in an siRNA can include all of the structural components, and/or all of the nucleotides of the siRNA molecule.

Examples of modified and chemically-modified siRNAs include siRNAs having modification of the sugar group of a nucleotide, modification of a nucleobase of a nucleotide, modification of a nucleic acid backbone or linkage, modification of the structure of a nucleotide or nucleotides at the terminus of a siRNA strand, and combinations thereof.

Examples of modified and chemically-modified siRNAs include siRNAs having modification of the substituent at the 2' carbon of the sugar.

Examples of modified and chemically-modified siRNAs include siRNAs having modification at the 5' end, the 3' end, or at both ends of a strand.

Examples of modified and chemically-modified siRNAs include siRNAs having modifications that produce complementarity mismatches between the strands.

Examples of modified and chemically-modified siRNAs include siRNAs having a 5'-propylamine end, a 5'-phosphorylated end, a 3'-puromycin end, or a 3'-biotin end group.

Examples of modified and chemically-modified siRNAs include siRNAs having a 2'-fluoro substituted ribonucleotide, a 2'-OMe substituted ribonucleotide, a 2'-deoxy ribonucleotide, a 2'-amino substituted ribonucleotide, a 2'-thio substituted ribonucleotide.

Examples of modified and chemically-modified siRNAs include siRNAs having one or more 5-halouridines, 5-halocytidines, 5-methylcytidines, ribothymidines, 2-aminopurines, 2,6-diaminopurines, 4-thiouridines, or 5-aminoallyluridines.

Examples of modified and chemically-modified siRNAs include siRNAs having one or more phosphorothioate groups.

Examples of modified and chemically-modified siRNAs include siRNAs having one or more 2'-fluoro substituted ribonucleotides, 2'-fluorouridines, 2'-fluorocytidines, 2'-deoxyribonucleotides, 2'-deoxyadenosines, or 2'-deoxyguanosines.

Examples of modified and chemically-modified siRNAs include siRNAs having one or more phosphorothioate linkages.

Examples of modified and chemically-modified siRNAs include siRNAs having one or more alkylene diol linkages, oxy-alkylthio linkages, or oxycarbonyloxy linkages.

Examples of modified and chemically-modified siRNAs include siRNAs having one or more deoxyabasic groups, inosines, N3-methyl-uridines, N6,N6-dimethyl-adenosines, pseudouridines, purine ribonucleosides, and ribavirins.

Examples of modified and chemically-modified siRNAs include siRNAs having one or more 3' or 5' inverted terminal groups.

Examples of modified and chemically-modified siRNAs include siRNAs having one or more 5-(2-amino)propyluridines, 5-bromouridines, adenosines, 8-bromo guanosines, 7-deaza-adenosines, or N6-methyl adenosine.

Methods for Modulating GST-π and Treating Malignant Tumor

Embodiments of this invention can provide RNAi molecules that can be used to down regulate or inhibit the expression of GST-π and/or GST-π proteins.

In some embodiments, a RNAi molecule of this invention can be used to down regulate or inhibit the expression of GST-π and/or GST-π proteins arising from GST-π haplotype polymorphisms that may be associated with a disease or condition such as malignant tumor.

Monitoring of GST-π protein or mRNA levels can be used to characterize gene silencing, and to determine the efficacy of compounds and compositions of this invention.

The RNAi molecules of this disclosure can be used individually, or in combination with other siRNAs for modulating the expression of one or more genes.

The RNAi molecules of this disclosure can be used individually, or in combination, or in conjunction with other known drugs for preventing or treating diseases, or ameliorating symptoms of conditions or disorders associated with GST-π, including malignant tumor.

The RNAi molecules of this invention can be used to modulate or inhibit the expression of GST-π in a sequence-specific manner.

The RNAi molecules of this disclosure can include a guide strand for which a series of contiguous nucleotides are at least partially complementary to a GST-π mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by determining the level of GST-π mRNA or the level of GST-π protein in cells of affected tissue.

Treatment of malignant tumor may be characterized by non-invasive medical scanning of an affected organ or tissue.

Embodiments of this invention may include methods for preventing, treating, or ameliorating the symptoms of a GST-π associated disease or condition in a subject in need thereof.

In some embodiments, methods for preventing, treating, or ameliorating the symptoms of malignant tumor in a subject can include administering to the subject a RNAi molecule of this invention to modulate the expression of a GST-π gene in the subject or organism.

In some embodiments, this invention contemplates methods for down regulating the expression of a GST-π gene in a cell or organism, by contacting the cell or organism with a RNAi molecule of this invention.

Embodiments of this invention encompass siRNA molecules of Tables 1-6 that are modified or chemically-modified according to the examples above.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of 2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797; Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A double stranded RNA (dsRNA) that is a Dicer substrate can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

In certain embodiments, the longest strand in a Dicer substrate dsRNA may be 24-30 nucleotides in length.

A Dicer substrate dsRNA can be symmetric or asymmetric.

In some embodiments, a Dicer substrate dsRNA can have a sense strand of 22-28 nucleotides and an antisense strand of 24-30 nucleotides.

In certain embodiments, a Dicer substrate dsRNA may have an overhang on the 3' end of the antisense strand.

In further embodiments, a Dicer substrate dsRNA may have a sense strand 25 nucleotides in length, and an antisense strand 27 nucleotides in length, with a 2 base 3'-overhang. The overhang may be 1, 2 or 3 nucleotides in length. The sense strand may also have a 5' phosphate.

An asymmetric Dicer substrate dsRNA may have two deoxyribonucleotides at the 3'-end of the sense strand in place of two of the ribonucleotides.

The sense strand of a Dicer substrate dsRNA may be from about 22 to about 30, or from about 22 to about 28; or from about 24 to about 30; or from about 25 to about 30; or from about 26 to about 30; or from about 26 and 29; or from about 27 to about 28 nucleotides in length.

The sense strand of a Dicer substrate dsRNA may be 22, 23, 24, 25, 26, 27, 28, 29 or 30 nucleotides in length.

In certain embodiments, a Dicer substrate dsRNA may have sense and antisense strands that are at least about 25 nucleotides in length, and no longer than about 30 nucleotides in length.

In certain embodiments, a Dicer substrate dsRNA may have sense and antisense strands that are 26 to 29 nucleotides in length.

In certain embodiments, a Dicer substrate dsRNA may have sense and antisense strands that are 27 nucleotides in length.

The sense and antisense strands of a Dicer substrate dsRNA may be the same length as in being blunt ended, or different lengths as in having overhangs, or may have a blunt end and an overhang.

A Dicer substrate dsRNA may have a duplex region of 19, 20, 21, 22, 23, 24, 25, 26 or 27 nucleotides in length.

The antisense strand of a Dicer substrate dsRNA may have any sequence that anneals to at least a portion of the sequence of the sense strand under biological conditions, such as within the cytoplasm of a eukaryotic cell.

A Dicer substrate with a sense and an antisense strand can be linked by a third structure, such as a linker group or a linker oligonucleotide. The linker connects the two strands of the dsRNA, for example, so that a hairpin is formed upon annealing.

The sense and antisense strands of a Dicer substrate are in general complementary, but may have mismatches in base pairing.

In some embodiments, a Dicer substrate dsRNA can be asymmetric such that the sense strand has 22-28 nucleotides and the antisense strand has 24-30 nucleotides.

A region of one of the strands, particularly the antisense strand, of the Dicer substrate dsRNA may have a sequence length of at least 19 nucleotides, wherein these nucleotides are in the 21-nucleotide region adjacent to the 3' end of the antisense strand and are sufficiently complementary to a nucleotide sequence of the RNA produced from the target gene.

An antisense strand of a Dicer substrate dsRNA can have from 1 to 9 ribonucleotides on the 5'-end, to give a length of 22-28 nucleotides. When the antisense strand has a length of 21 nucleotides, then 1-7 ribonucleotides, or 2-5 ribonucleotides, or 4 ribonucleotides may be added on the 3'-end. The added ribonucleotides may have any sequence.

A sense strand of a Dicer substrate dsRNA may have 24-30 nucleotides. The sense strand may be substantially complementary with the antisense strand to anneal to the antisense strand under biological conditions.

Methods for Using RNAi Molecules

The nucleic acid molecules and RNAi molecules of this invention may be delivered to a cell or tissue by direct application of the molecules, or with the molecules combined with a carrier or a diluent.

The nucleic acid molecules and RNAi molecules of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of this invention can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

Example Protocol for In Vitro Knockdown

One day before the transfection, cells were plated in a 96-well plate at 2×10³ cells per well with 100 µl of DMEM (HyClone Cat. #SH30243.01) containing 10% FBS and culture in a 37° C. incubator containing a humidified atmosphere of 5% CO2 in air. Before transfection, medium was changed to 90 µl of Opti-MEM I Reduced Serum Medium (Life Technologies Cat. #31985-070) containing 2% FBS. Then, 0.2 µl of Lipofectamine RNAiMax (Life Technologies Cat. #13778-100) was mixed with 4.8 µl of Opti-MEM I for 5 minutes at room temperature. Next, 1 µl of siRNA was mixed with 4 µl of Opti-MEM I and combined with the LF2000 solution, and mixed gently, without vortex. After 5 minutes at room temperature, the mixture was incubated for an additional 10 minutes at room temperature to allow the RNA-RNAiMax complexes to form. Further, the 10 µl of RNA-RNAiMax complexes was added to a well, and the plate was shaken gently by hand. The cells were incubated in a 37° C. incubator containing a humidified atmosphere of 5% CO2 in air for 2 hours. The medium was changed to fresh Opti-MEM I Reduced Serum Medium containing 2% FBS. 24 hours after transfection, the cells were washed with ice-cold PBS once. The cells were lysed with 50 µl of Cell-to-Ct Lysis Buffer (Life Technologies Cat. #4391851 C) for 5-30 minutes at room temperature. 5 µl of Stop Solution was added, and it was incubated for 2 minutes at room temperature. The mRNA level was measured by RT-qPCR with TAQMAN immediately. Samples could be frozen at −80° C. and assayed at a later time.

Example Protocol for Serum Stability 0.2 mg/ml siRNA was incubated with 10% human serum at 37° C. At certain time points (0, 5, 15 and 30 min), 200 µl of sample was aliquoted and extracted with 200 µl extraction solvent (Chloroform:phenol:Isoamyl alcohol=24:25:1). The sample was vortexed and centrifuged at 13,000 rpm for 10 min at RT, then the top layer solution was transferred and filtered it with 0.45 µm filter. The filtrate was transferred into a 300 µl HPLC injection vial. For LCMS, the Mobile phase was MPA: 100 mM HFIP+7 mM TEA in H2O, MPB: 50% Methanol+50% Acetonitrile. The Column:Waters Acquity OST 2.1×50 mm, 1.7 µm.

EXAMPLES

Example 1 siRNAs of this invention targeted to GST-π were found to be active for gene silencing in vitro. The dose-dependent activities of GST-π siRNAs for gene knockdown were found to exhibit an IC50 below about 250 picomolar (pM), and as low as 1 pM.

In vitro transfection was performed in an A549 cell line to determine siRNA knockdown efficacy. Dose dependent knockdown for GST-π mRNA was observed with siRNAs of Table 1, as shown in Table 7.

TABLE 7

Dose dependent knockdown for GST-π mRNA in an A549 cell line

| siRNA structure | IC50 (pM) |
| --- | --- |
| A9 (SEQ ID NOs: 25 and 90) | 24 |
| B2 (SEQ ID NOs: 52 and 117) | 121 |
| B3 (SEQ ID NOs: 53 and 118) | 235 |
| B4 (SEQ ID NOs: 54 and 119) | 229 |
| B13 (SEQ ID NOs: 50 and 115) | 17 |
| BU2 (SEQ ID NOs: 61 and 126) | 31 |

As shown in Table 7, the activities of GST-π siRNAs of Table 1 were in the range 17-235 pM, which is suitable for many uses, including as a drug agent to be used in vivo.

Example 2

The structure of GST-π siRNAs of this invention having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure BU2' (SEQ ID NOs:131 and 157). Dose dependent knockdown of GST-π mRNA was observed with GST-π siRNAs based on structure BU2' as shown in Table 8.

TABLE 8

Dose dependent knockdown of GST-π mRNA in an A549 cell line for GST-π siRNAs based on structure BU2'

| GST-π siRNA structure | IC50 (pM) |
| --- | --- |
| BU2 with no deoxynucleotides in the duplex region (SEQ ID NOs: 61 and 126) | 31 |
| BU2 with deoxynucleotides in positions 3, 5, and 7 of the seed region antisense strand (SEQ ID NOs: 139 and 165) | 5 |
| BU2 with deoxynucleotides in positions 4, 6, and 8 of the seed region antisense strand (SEQ ID NOs: 141 and 167) | 8 |
| BU2 with deoxynucleotides in positions 4, 6, and 8 of the seed region antisense strand (SEQ ID NOs: 156 and 182) | 5 |

As shown in Table 8, the activities of GST-π siRNAs based on structure BU2' having three deoxynucleotides in the seed region of the antisense strand were surprisingly and unexpectedly increased by up to 6-fold, as compared to a GST-π siRNA without deoxynucleotides in the duplex region.

These data show that GST-π siRNAs having a structure with three deoxynucleotides located at positions 3, 5 and 7, or at positions 4, 6 and 8 in the seed region of the antisense strand provided surprisingly increased gene knockdown activity as compared to a GST-π siRNA without deoxynucleotides in the duplex region.

The activities shown in Table 8 for GST-π siRNAs having three deoxynucleotides in the seed region of the antisense strand were in the range 5 to 8 pM, which is exceptionally suitable for many uses, including as a drug agent to be used in vivo.

Example 3

The structure of GST-π siRNAs of this invention having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure A9' (SEQ ID NOs:183 and 195). Dose dependent knockdown of GST-π mRNA was observed with the GST-π siRNAs based on structure A9', as shown in Table 9.

TABLE 9

Dose dependent knockdown of GST-π mRNA in an A549 cell line for GST-π siRNAs based on structure structure A9'

| GST-π siRNA structure | IC50 (pM) |
|---|---|
| A9 with no deoxynucleotides in the duplex region (SEQ ID NOs: 25 and 90) | 24 |
| A9 with deoxynucleotides in positions 4, 6, and 8 of the seed region antisense strand (SEQ ID NOs: 193 and 205) | 1 |
| A9 with deoxynucleotides in positions 1, 3, 5, and 7 of the seed region antisense strand (SEQ ID NOs: 190 and 202) | 5 |
| A9 with deoxynucleotides in positions 3-8 of the seed region antisense strand (SEQ ID NOs: 187 and 199) | 6 |
| A9 with deoxynucleotides in positions 5-8 of the seed region antisense strand (SEQ ID NOs: 189 and 201) | 7 |
| A9 with deoxynucleotides in positions 3, 5, and 7 of the seed region antisense strand (SEQ ID NOs: 191 and 203) | 15 |

As shown in Table 9, the activities of GST-π siRNAs based on structure A9' having three to six deoxynucleotides in the seed region of the antisense strand were surprisingly increased by up to 24-fold, as compared to a GST-π siRNA without deoxynucleotides in the duplex region.

These data show that GST-π siRNAs having a structure with three to six deoxynucleotides located at positions 4, 6 and 8, or at positions 1, 3, 5 and 7, or at positions 3-8, or at positions 5-8, or at positions 3, 5 and 7 in the seed region of the antisense strand provided unexpectedly increased gene knockdown activity as compared to a GST-π siRNA without deoxynucleotides in the duplex region.

The activity shown in Table 9 for GST-π siRNAs having three to six deoxynucleotides in the seed region of the antisense strand was in the range 1 to 15 pM, which is exceptionally suitable for many uses, including as a drug agent to be used in vivo.

Example 4

The structure of GST-π siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B13' (SEQ ID NOs:207 and 222). Dose dependent knockdown of GST-π mRNA was observed with the GST-π siRNAs based on structure B13', as shown in Table 10.

TABLE 10

Dose dependent knockdown of GST-π mRNA in an A549 cell line for GST-π siRNAs based on structure B13'

| GST-π siRNA structure | IC50 (pM) |
|---|---|
| B13 with no deoxynucleotides in the duplex region (SEQ ID NOs: 50 and 115) | 17 |
| B13 with deoxynucleotides in positions 4, 6, and 8 of the seed region antisense strand (SEQ ID NOs: 217 and 232) | 11 |

As shown in Table 10, the activity of a GST-π siRNA based on structure B13' having three deoxynucleotides in the seed region of the antisense strand was unexpectedly increased, as compared to a GST-π siRNA without deoxynucleotides in the duplex region.

These data show that GST-π siRNAs having a structure with three deoxynucleotides located at positions 4, 6 and 8 in the seed region of the antisense strand provided unexpectedly increased gene knockdown activity as compared to a GST-π siRNA without deoxynucleotides in the duplex region.

The activity shown in Table 10 for GST-π siRNAs having three deoxynucleotides in the seed region of the antisense strand was in the picomolar range at 11 pM, which is exceptionally suitable for many uses, including as a drug agent to be used in vivo.

Example 5

The structure of GST-π siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B4' (SEQ ID NOs:261 and 273). Dose dependent knockdown of GST-π mRNA was observed with the GST-π siRNAs based on structure B4', as shown in Table 11.

TABLE 11

Dose dependent knockdown of GST-π mRNA in an A549 cell line for GST-π siRNAs based on structure B4'

| GST-π siRNA structure | IC50 (pM) |
|---|---|
| B4 with no deoxynucleotides in the duplex region (SEQ ID NOs: 54 and 119) | 229 |
| B4 with deoxynucleotides in positions 3-8 of the seed region antisense strand (SEQ ID NOs: 265 and 277) | 113 |

As shown in Table 11, the activities of GST-π siRNAs based on structure B4' having six deoxynucleotides in the seed region of the antisense strand were unexpectedly increased by more than two-fold, as compared to a GST-π siRNA without deoxynucleotides in the duplex region.

These data show that GST-π siRNAs having a structure with six deoxynucleotides located at positions 3-8 in the seed region of the antisense strand provided surprisingly increased gene knockdown activity as compared to a GST-π siRNA without deoxynucleotides in the duplex region.

The activity shown in Table 11 for a GST-π siRNA having six deoxynucleotides in the seed region of the antisense strand was in the picomolar range at 113 pM, which is exceptionally suitable for many uses, including as a drug agent to be used in vivo.

Example 6

The structure of GST-π siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B2' (SEQ ID NOs:237 and 249). Dose dependent knockdown of GST-π mRNA was observed with the GST-π siRNAs based on structure B2', as shown in Table 12.

TABLE 12

Dose dependent knockdown of GST-π mRNA in an A549 cell line for GST-π siRNAs based on structure B2'

| GST-π siRNA structure | IC50 (pM) |
|---|---|
| B2 with no deoxynucleotides in the duplex regioin (SEQ ID NOs: 52 and 117) | 121 |
| B2 with deoxynucleotides in positions 5-8 of the seed region antisense strand (SEQ ID NOs: 243 and 255) | 30 |
| B2 with deoxynucleotides in positions 1, 3, 5, and 7 of the seed region antisense strand (SEQ ID NOs: 244 and 256) | 50 |
| B2 with deoxynucleotides in positions 3, 5, and 7 of the seed region antisense strand (SEQ ID NOs: 245 and 257) | 100 |

As shown in Table 12, the activities of GST-π siRNAs based on structure B2' having three to four deoxynucleotides in the seed region of the antisense strand were surprisingly increased by up to 4-fold, as compared to a GST-π siRNA without deoxynucleotides in the duplex region.

These data show that GST-π siRNAs having a structure with three to four deoxynucleotides located at positions 5-8, or at positions 1, 3, 5 and 7, or at positions 3, 5 and 7 in the seed region of the antisense strand provided unexpectedly increased gene knockdown activity as compared to a GST-π siRNA without deoxynucleotides in the duplex region.

The activities shown in Table 12 for GST-π siRNAs having three to four deoxynucleotides in the seed region of the antisense strand were in the range 30-100 pM, which is exceptionally suitable for many uses, including as a drug agent to be used in vivo.

Example 7

The structure of GST-π siRNAs containing one or more 2'-deoxy-2'-fluoro substituted nucleotides provided unexpectedly increased gene knockdown activity in vitro.

In vitro transfection was performed in an A549 cell line to determine knockdown efficacy for GST-π siRNAs based on structure BU2' (SEQ ID NOs:131 and 157). Dose dependent knockdown of GST-π mRNA was observed with the GST-π siRNAs based on structure BU2', as shown in Table 13.

TABLE 13

Dose dependent knockdown of GST-π mRNA in an A549 cell line for GST-π siRNAs based on structure BU2'

| GST-π siRNA structure | IC50 (pM) |
|---|---|
| BU2 with no 2'-F deoxynucleotides (SEQ ID NOs: 61 and 126) | 31 |
| BU2 with seven 2'-F deoxynucleotides, one in position 1 at the 3' end of the antisense strand (SEQ ID NOs: 148 and 174) | 3 |
| BU2 with four 2'-F deoxynucleotides, one in position 1 at the 3' end of the antisense strand (SEQ ID NOs: 147 and 173) | 11 |
| BU2 with one 2'-F deoxynucleotide in position 1 at the 3' end of the antisense strand (SEQ ID NOs: 144 and 170) | 13 |

As shown in Table 13, the activities of GST-π siRNAs based on structure BU2' having one or more 2'-F deoxynucleotides were surprisingly increased by up to 10-fold, as compared to a GST-π siRNA without 2'-F deoxynucleotides.

These data show that GST-π siRNAs having a structure with one or more 2'-F deoxynucleotides provided unexpectedly increased gene knockdown activity as compared to a GST-π siRNA without a 2'-F deoxynucleotide.

The activities shown in Table 13 for GST-π siRNAs having one or more 2'-F deoxynucleotides were in the range 3 to 13 pM, which is exceptionally suitable for many uses, including as a drug agent to be used in vivo.

Example 8

The structure of GST-π siRNAs containing one or more 2'-deoxy-2'-fluoro substituted nucleotides provided unexpectedly increased gene knockdown activity in vitro.

In vitro transfection was performed in an A549 cell line to determine knockdown efficacy for GST-π siRNAs based on structure B13' (SEQ ID NOs:207 and 222). Dose dependent knockdown of GST-π mRNA was observed with the GST-π siRNAs based on structure B 13', as shown in Table 14.

TABLE 14

Dose dependent knockdown of GST-π mRNA in an A549 cell line for GST-π siRNAs based on structure B13'

| GST-π siRNA structure | IC50 (pM) |
|---|---|
| B13 with no 2'-F deoxynucleotides (SEQ ID NOs: 50 and 115) | 17 |
| B13 with three 2'-F deoxynucleotides located in non-overhang positions (SEQ ID NOs: 219 and 234) | 6 |

As shown in Table 14, the activity of a GST-π siRNA based on structure B13' having three 2'-F deoxynucleotides located in non-overhang positions was surprisingly increased by about 3-fold, as compared to a GST-π siRNA without 2'-F deoxynucleotides.

These data show that GST-π siRNAs having a structure with one or more 2'-F deoxynucleotides provided unexpectedly increased gene knockdown activity as compared to a GST-π siRNA without a 2'-F deoxynucleotide.

The activity shown in Table 14 for GST-π siRNAs having one or more 2'-F deoxynucleotides was in the picomolar range at 6 pM, which is exceptionally suitable for many uses, including as a drug agent to be used in vivo.

Example 9: Orthotopic A549 Lung Cancer Mouse Model

The GST-π siRNAs of this invention can exhibit profound reduction of orthotopic lung cancer tumors in vivo. In this example, a GST-π siRNA provided gene knockdown potency in vivo when administered in a liposomal formulation to the orthotopic lung cancer tumors in athymic nude mice.

In general, an orthotopic tumor model can exhibit direct clinical relevance for drug efficacy and potency, as well as improved predictive ability. In the orthotopic tumor model, tumor cells are implanted directly into the same kind of organ from which the cells originated.

The anti-tumor efficacy of the siRNA formulation against human lung cancer A549 was evaluated by comparing the final primary tumor weights measured at necropsy for the treatment group and the vehicle control group.

FIG. 1 shows orthotopic lung cancer tumor inhibition in vivo for a GST-π siRNA based on structure BU2 (SEQ ID NOs:61 and 126). An orthotopic A549 lung cancer mouse model was utilized with a relatively low dose at 2 mg/kg of the siRNA targeted to GST-π.

The GST-π siRNA showed significant and unexpectedly advantageous lung tumor inhibition efficacy in this six-week study. As shown in FIG. 1, after 43 days, the GST-π siRNA showed markedly advantageous tumor inhibition efficacy, with final tumor average weights significantly reduced by 2.8-fold as compared to control.

For this study, male NCr nu/nu mice, 5-6 weeks old, were used. The experimental animals were maintained in a HEPA filtered environment during the experimental period. The siRNA formulations were stored at 4° C. before use, and warmed to room temperature 10 minutes prior to injection in mouse.

For this A549 human lung cancer orthotopic model, on the day of surgical orthotopic implantation (SOI), the stock tumors were harvested from the subcutaneous site of animals bearing A549 tumor xenograft and placed in RPMI-1640 medium. Necrotic tissues were removed and viable tissues were cut into 1.5-2 mm$^3$ pieces. The animals were anesthetized with isoflurane inhalation and the surgical area was sterilized with iodine and alcohol. A transverse incision approximately 1.5 cm long was made in the left chest wall of the mouse using a pair of surgical scissors. An intercostal incision was made between the third and the fourth rib and the left lung was exposed. One A549 tumor fragment was transplanted to the surface of the lung with an 8-0 surgical suture (nylon). The chest wall was closed with a 6-0 surgical suture (silk). The lung was re-inflated by intrathoracic puncture using a 3 cc syringe with a 25 G×1½ needle to draw out the remaining air in the chest cavity. The chest wall was closed with a 6-0 surgical silk suture. All procedures of the operation described above were performed with a 7× magnification microscope under HEPA filtered laminar flow hoods.

Three days after tumor implantation, the model tumor-bearing mice were randomly divided into groups of ten mice per group. For the group of interest, treatment of the ten mice was initiated three days after tumor implantation.

For the group of interest, the formulation was (Ionizable lipid:cholesterol:DOPE:DOPC:DPPE-PEG-2K:D SPE-PEG-2K), a liposomal composition. The liposomes encapsulated the GST-π siRNA.

For the study endpoint, the experimental mice were sacrificed forty-two days after treatment initiation. Primary tumors were excised and weighed on an electronic balance for subsequent analysis.

For an estimation of compound toxicity, the mean body weight of the mice in the treated and control groups was maintained within the normal range during the entire experimental period. Other symptoms of toxicity were not observed in the mice.

Example 10

The GST-π siRNAs of this invention exhibited profound reduction of cancer xenograft tumors in vivo. The GST-π siRNAs provided gene knockdown potency in vivo when administered in a liposomal formulation to the cancer xenograft tumors.

Figure 2:
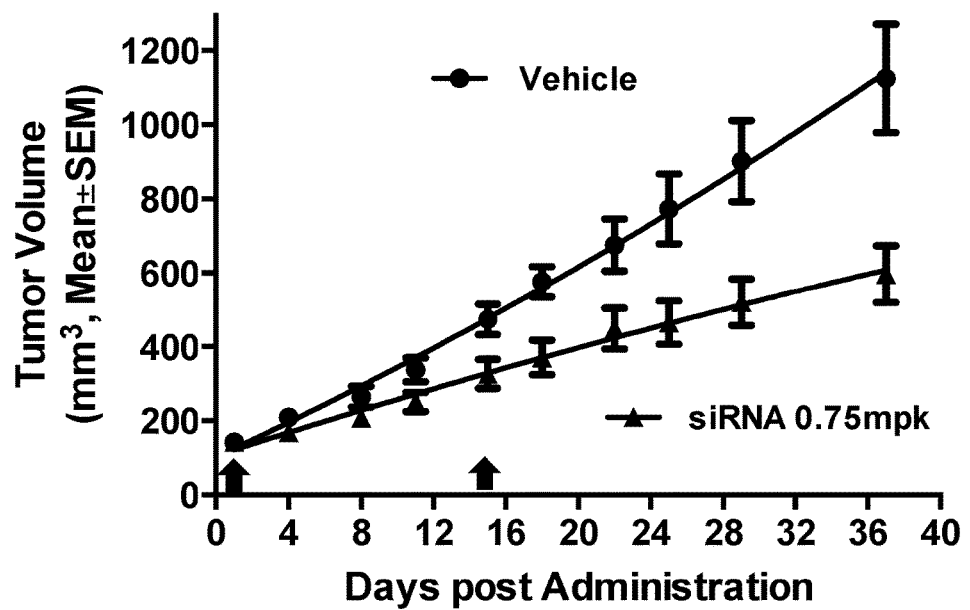
FIG. 2 shows tumor inhibition efficacy in vivo for a GST-π siRNA. A cancer xenograft model using A549 cells was utilized with a relatively low dose of siRNA at 0.75 mg/kg. The GST-π siRNA showed advantageous tumor inhibition within a few days. After 36 days, the GST-π siRNA showed markedly advantageous tumor inhibition, with final tumor average volumes significantly reduced by about 2-fold, as compared to control.

FIG. 2 shows tumor inhibition efficacy for a GST-π siRNA (SEQ ID Nos:156 and 182). A cancer xenograft model was utilized with a relatively low dose at 0.75 mg/kg of siRNA targeted to GST-π.

The GST-π siRNA showed significant and unexpectedly advantageous tumor inhibition efficacy within a few days after administration. After 36 days, the GST-π siRNA showed markedly advantageous tumor inhibition efficacy, with tumor volume reduced by 2-fold as compared to control.

Figure 3:
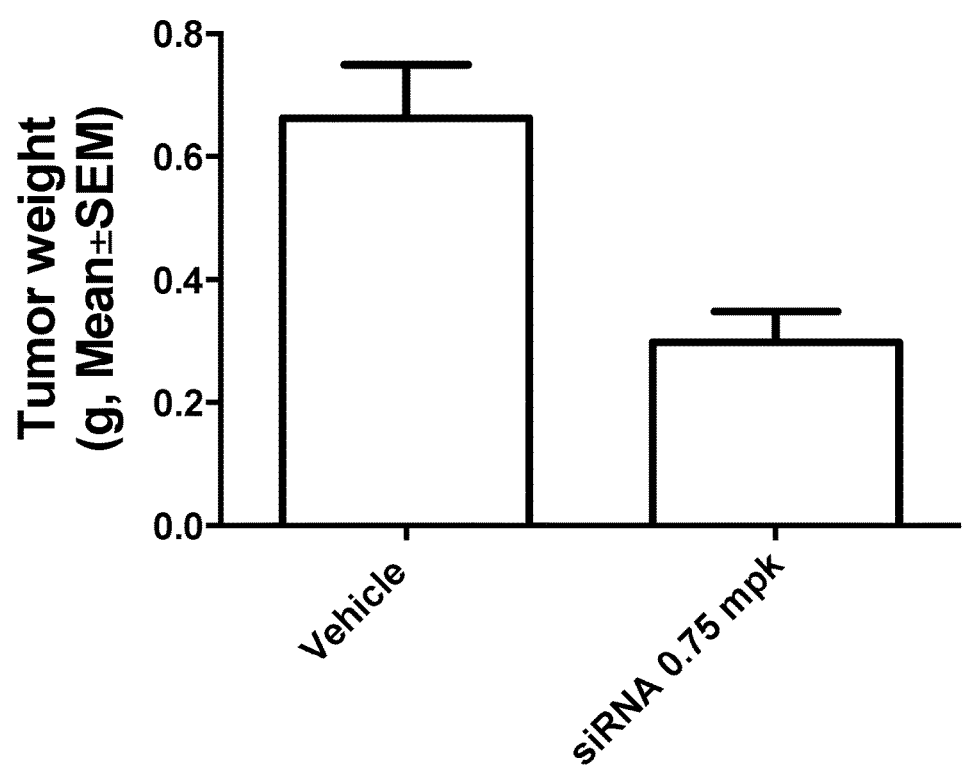
FIG. 3 shows tumor inhibition efficacy in vivo for a GST-π siRNA at the endpoint of FIG. 2. The GST-π siRNA showed advantageous tumor inhibition with average tumor weights reduced by more than 2-fold.

As shown in FIG. 3, the GST-π siRNA demonstrated significant and unexpectedly advantageous tumor inhibition efficacy at the endpoint day. In particular, tumor weight was reduced by more than 2-fold.

The GST-π siRNA was administered in two injections (day 1 and 15) of a liposomal formulation having the composition (Ionizable lipid:Cholesterol:DOPE:DOPC:DPPE-PEG-2K) (25:30:20:20:5).

For the cancer xenograft model, an A549 cell line was obtained from ATCC. The cells were maintained in culture medium supplemented with 10% Fetal Bovine Serum and 100 U/ml penicillin and 100 µg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of 5×10$^7$/ml in media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 7-8 mice per group.

For tumor model preparation, each mouse was inoculated subcutaneously in the right flank with 0.1 ml an inoculum of 2.5×10$^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Once the established tumors reached approximately 120-175 mm$^3$, average tumor volume was about 150 mm$^3$, the mice were assigned into the various vehicle control and treatment groups such that the mean tumor volumes in the treated groups were within 10% of the mean tumor volume in the vehicle control group, ideally, the CV % of tumor volume was less than 25%. On the same day, test articles and control vehicle were administered according to the dosing regimen. Tumor volumes were monitored three times for week 1, twice for the rest of weeks, including the day of study termination.

For dosage administration, on the dosing day, the test articles were taken out from −80° C. freezer and thawed on ice. Before applied to syringes, the bottle containing formulation was reverted by hands for a few times. All test articles were dosed at 0.75 mg/kg by IV, q2w×2, at 10 ml/kg.

For body weight, mice were weighed to the nearest 0.1 g. Body weights were monitored and recorded daily within 7 days post dosing for first dose. Body weights were monitored and recorded twice for weeks, for the rest of weeks, including the day of study termination.

For tumors collection, on 28 days post first dosing, tumor volume was measured, and tumor was dissected for weight measurement, and stored for PD biomarker study. Tumor weight was recorded.

Example 11

The GST-π siRNAs of this invention demonstrated increased cancer cell death by apoptosis of cancer cells in vitro. The GST-π siRNAs provided GST-π knockdown, which resulted in upregulation of PUMA, a biomarker for apoptosis and associated with loss in cell viability.

GST-π siRNA SEQ ID NOs:156 and 182, which contained a combination of deoxynucleotides in the seed region, a 2'-F substituted deoxynucleotide, and 2'-OMe substituted ribonucleotides, provided unexpectedly increased apoptosis of cancer cells.

Figure 4:
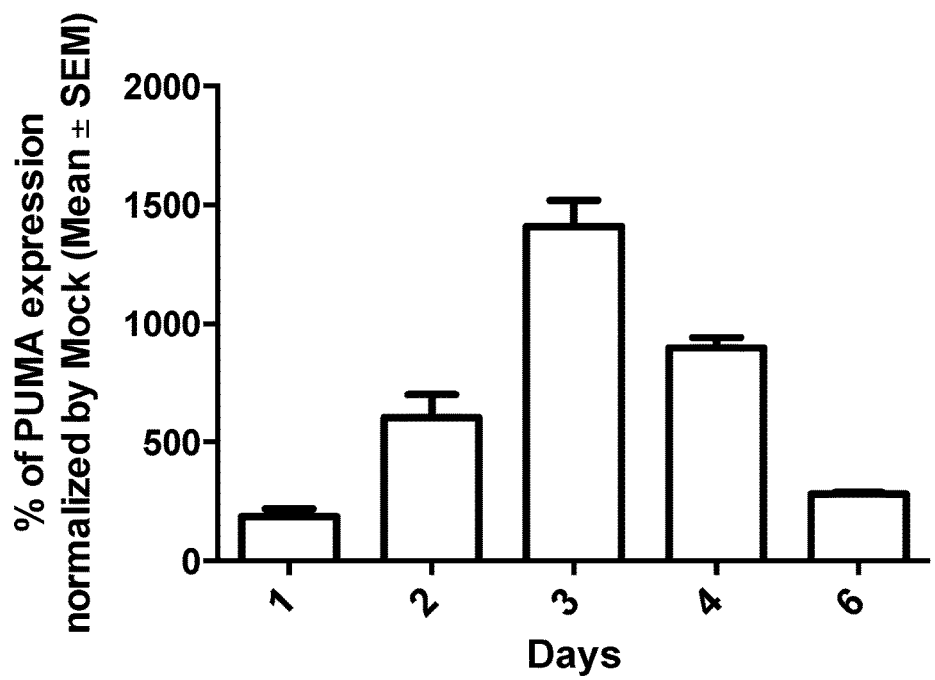
FIG. 4 shows that a GST-π siRNA of this invention greatly increased cancer cell death by apoptosis in vitro. The GST-π siRNA caused upregulation of PUMA, a biomarker for apoptosis, which is associated with loss in cell viability.

The level of expression of PUMA for GST-π siRNA SEQ ID NOs:156 and 182 was measured as shown in FIG. 4. In FIG. 4, the expression of PUMA was greatly increased from 2-4 days after transfection of the GST-π siRNA.

These data show that the structure of GST-π siRNAs containing a combination of deoxynucleotides in the seed region, a 2'-F substituted deoxynucleotide, and 2'-OMe substituted ribonucleotides provided unexpectedly increased apoptosis of cancer cells.

The protocol for the PUMA biomarker was as follows. One day before transfection, cells were plated in a 96-well plate at $2 \times 10^3$ cells per well with 100 µl of DMEM (Hy-Clone Cat. #SH30243.01) containing 10% FBS and cultured in a 37° C. incubator containing a humidified atmosphere of 5% CO2 in air. Next day, before transfection the medium was replaced with 90 µl of Opti-MEM I Reduced Serum Medium (Life Technologies Cat. #31985-070) containing 2% FBS. Then, 0.2 µl of Lipofectamine RNAiMAX (Life Technologies Cat. #13778-100) were mixed with 4.8 µl of Opti-MEM I for 5 minutes at room temperature. 1 µl of the GST-π siRNA (stock conc. 1 µM) was mixed with 4 µl of Opti-MEM I and combined with the RNAiMAX solution and then mixed gently. The mixture was incubated for 10 minutes at room temperature to allow the RNA-RNAiMAX complexes to form. 10 µl of RNA-RNAiMAX complexes were added per well, to final concentration of the siRNA 10 nM. The cells were incubated for 2 hours and medium changed to fresh Opti-MEM I Reduced Serum Medium containing 2% FBS. For 1, 2, 3, 4, and 6 days post transfection, the cells were washed with ice-cold PBS once and then lysed with 50 µl of Cell-to-Ct Lysis Buffer (Life Technologies Cat. #4391851 C) for 5-30 minutes at room temperature. 5 µl of Stop Solution was added and incubated for 2 minutes at room temperature. PUMA (BBC3, Cat#Hs00248075, Life Technologies) mRNA levels were measured by qPCR with TAQMAN.

Example 12

The GST-π siRNAs of this invention can exhibit profound reduction of cancer xenograft tumors in vivo. The GST-π siRNAs can provide gene knockdown potency in vivo when administered in a liposomal formulation to the cancer xenograft tumors.

Figure 5:
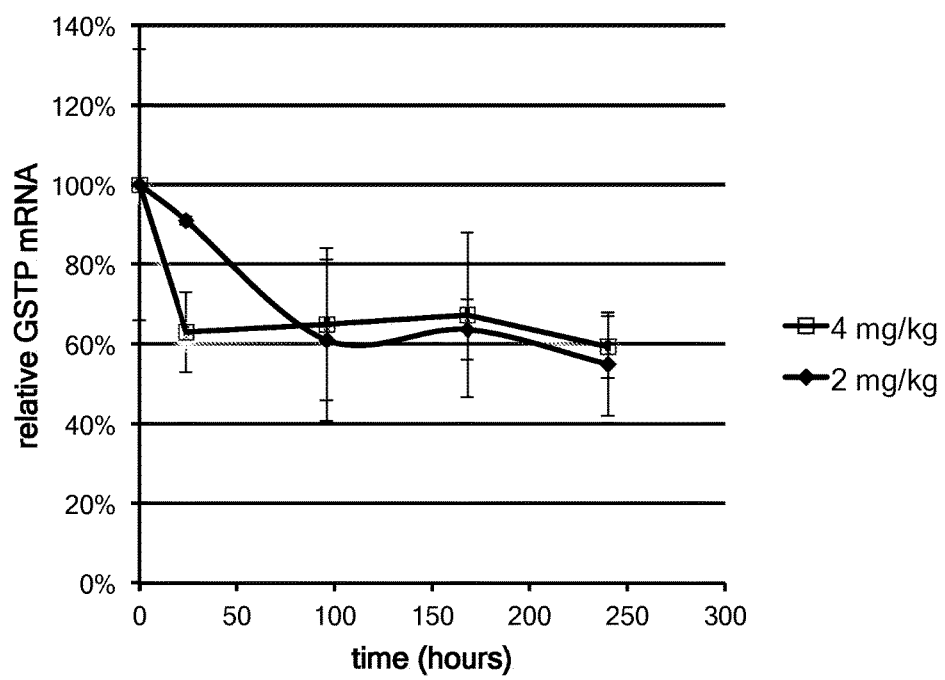
FIG. 5 shows that a GST-π siRNA of this invention provided knockdown efficacy for A549 xenograft tumors in vivo. Dose dependent knockdown of GST-π mRNA was observed in athymic nude (nu/nu) female mice (Charles River) with the siRNA targeted to GST-π.

FIG. 5 shows tumor inhibition efficacy for a GST-π siRNA (SEQ ID NOs:61 and 126). Dose dependent knockdown of GST-π mRNA was observed in vivo with the siRNA targeted to GST-π. A cancer xenograft model was utilized with a siRNA targeted to GST-π.

The GST-π siRNA showed significant and unexpectedly advantageous tumor inhibition efficacy within a few days after administration. As shown in FIG. 5, treatment with a GST-π siRNA resulted in significant reduction of GST-π mRNA expression 4 days after injection in a lipid formulation. At the higher dose of 4 mg/kg, significant reduction of about 40% was detected 24 hours after injection.

The GST-π siRNA was administered in a single injection of 10 mL/kg of a liposomal formulation having the composition (Ionizable lipid:Cholesterol:DOPE:DOPC:DPPE-PEG-2K) (25:30:20:20:5).

For the cancer xenograft model, an A549 cell line was obtained from ATCC. The cells were maintained in RPMI-1640 supplemented with 10% Fetal Bovine Serum and 100 U/ml penicillin and 100 µg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of $4 \times 10^7$/ml in RPMI media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 3 mice per group.

For tumor model preparation, each mouse was inoculated subcutaneously in the right flank with 0.1 ml an inoculum of $2 \times 10^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Tumor volumes were monitored twice a week. Once the established tumors reached approximately 350-600 mm$^3$, the mice were assigned into groups with varied time points. On the same day, test articles were administered according to the dosing regimen.

For dosage administration, on the day when the established tumors reached approximately 350-600 mm$^3$, the test articles were taken out from 4° C. fridge. Before being applied to syringes, the bottle containing formulation was reverted by hand for a few times to make a homogeneous solution.

For body weight, mice were weighed to the nearest 0.1 g. Body weights were monitored and recorded twice for weeks, for the rest of weeks, including the day of study termination.

For tumors collection, animals were sacrificed by overdosed CO$_2$ and tumors were dissected at 0, 24, 48, 72, 96(optional), and 168 hours following the dosing. Tumors were first wet weighted, and then separated into three parts for KD, distribution and biomarker analysis. The samples were snap frozen in liquid nitrogen and stored at −80° C. until ready to be processed.

Example 13

The GST-π siRNAs of this invention inhibited pancreatic cancer xenograft tumors in vivo. The GST-π siRNAs provided gene knockdown potency in vivo when administered in a liposomal formulation to the pancreatic cancer xenograft tumors.

In this xenograft model, each mouse was inoculated subcutaneously in the right flank with 0.1 ml an inoculum of $2.5 \times 10^6$ of PANC-1 cells. Athymic nude female mice, 6 to 8 weeks, Charles River, were used. Tumor size was measured to the nearest 0.1 mm. Once the established tumors reached approximately 150-250 mm³ (average tumor volume at about 200 mm³), the mice were assigned into the various vehicle control and treatment groups such that the mean tumor volumes in the treated groups were within 10% of the mean tumor volume in the vehicle control group. On the same day, test articles and control vehicle were administered according to the dosing regimen. Tumor volumes were monitored three times for week 1, twice for the rest of weeks, including the day of study termination.

Figure 6:
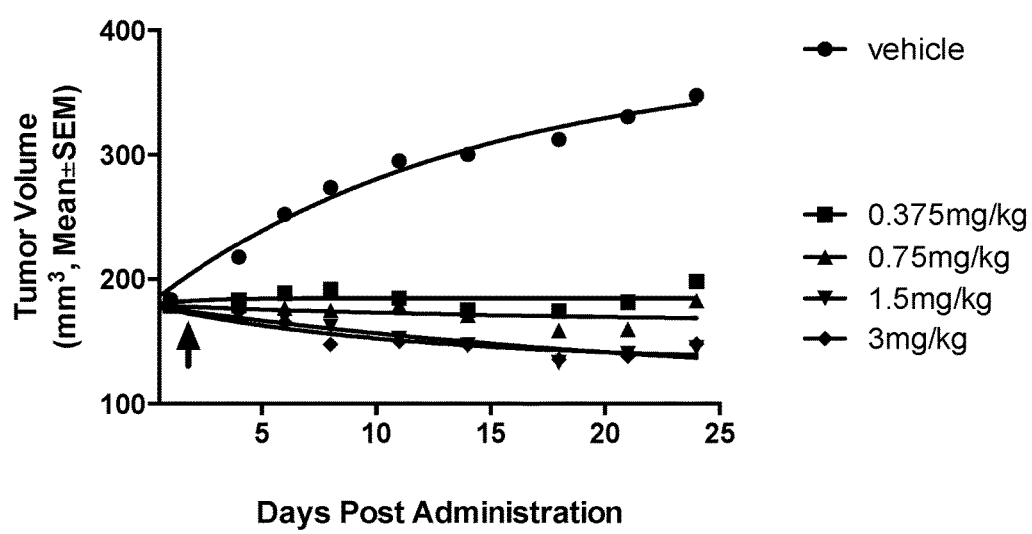
FIG. 6 shows that a GST-π siRNA of this invention inhibited pancreatic cancer xenograft tumors in vivo. The GST-π siRNA provided gene silencing potency in vivo when administered in a liposomal formulation to pancreatic cancer xenograft tumors in athymic nude female mice, 6 to 8 weeks old.

FIG. 6 shows tumor inhibition efficacy for a GST-π siRNA (SEQ ID Nos:61 and 126). As shown in FIG. 6, a dose response was obtained with doses ranging from 0.375 mg/kg to 3 mg/kg of siRNA targeted to GST-π. The GST-π siRNA showed significant and unexpectedly advantageous tumor inhibition efficacy within a few days after administration. Thus, the GST-π siRNA demonstrated significant and unexpectedly advantageous tumor inhibition efficacy at the endpoint.

The GST-π siRNAs were administered in a liposomal formulation having the composition (Ionizable lipid:cholesterol:DOPE:DOPC:DPPE-PEG-2K) (25:30:20:20:5).

Example 14

The GST-π siRNAs of this invention exhibited increased serum stability.

Figure 7:
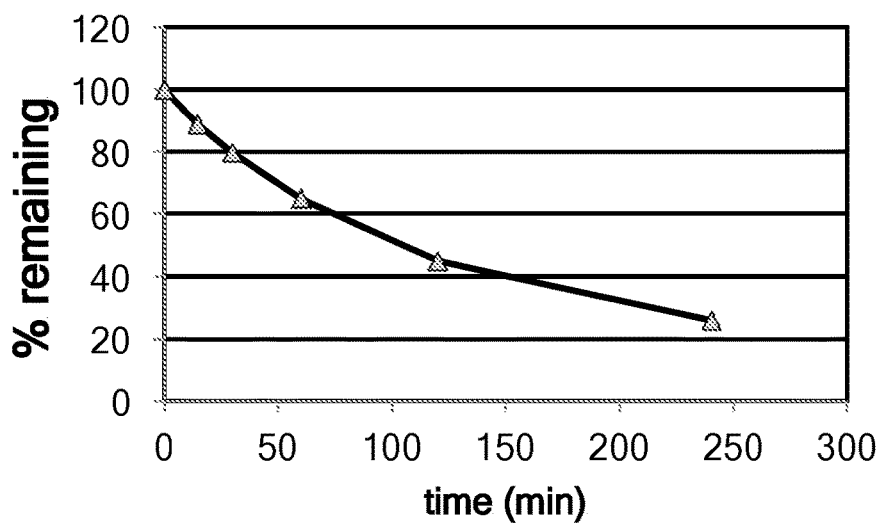
FIG. 7 shows that a GST-π siRNA of this invention exhibited increased serum stability.
Figure 7:
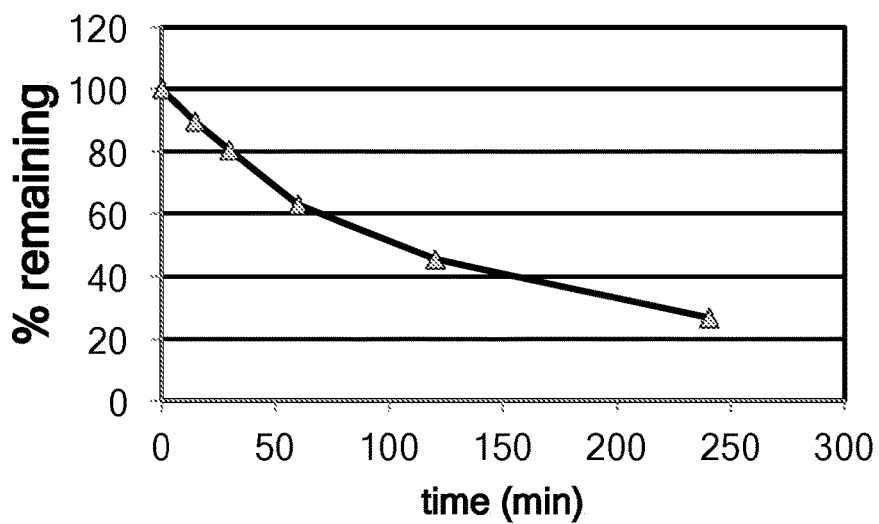

FIG. 7 shows incubation in human serum and detection of remaining siRNA at various time points by HPLS/LCMS. As shown in FIG. 7, the half-life ($t_{1/2}$) in serum for both the sense strand (FIG. 7, top) and antisense strand (FIG. 7, bottom) of a GST-π siRNA (SEQ ID Nos:61 and 126) was about 100 minutes.

Example 15

The GST-π siRNAs of this invention exhibited enhanced stability in formulation in plasma.

Figure 8:
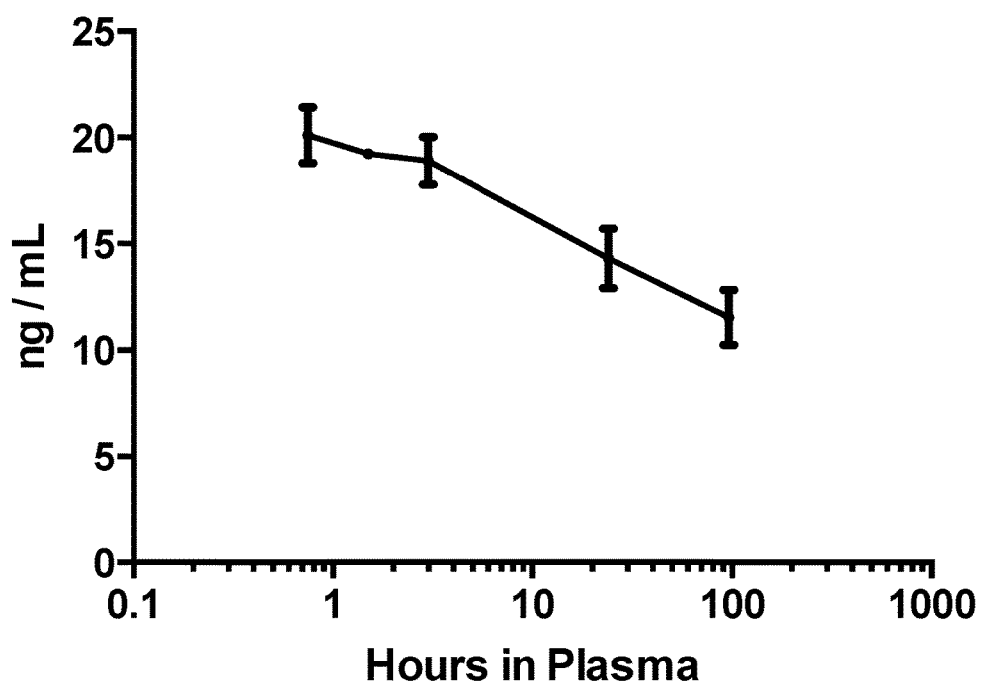
FIG. 8 shows that a GST-π siRNA of this invention exhibited enhanced stability in formulation in plasma.

FIG. 8 shows incubation of formulation in plasma and detection of remaining siRNA at various time points. As shown in FIG. 8, the half-life ($t_{1/2}$) in plasma of a formulation of GST-π siRNA (SEQ ID Nos:61 and 126) was significantly longer than 100 hours.

The GST-π siRNA was prepared in a liposomal formulation having the composition (Ionizing lipid:cholesterol:DOPE:DOPC:DPPE-PEG-2K) (25:30:20:20:5). The z-average size for the liposomal nanoparticles was 40.0 nm, and the siRNA was 91% encapsulated.

The formulation was incubated in 50% human serum in PBS for 40 min, 1.5 h, 3 h, 24 h, and 96 h. The amount of the GST-π siRNA was determined by an ELISA-based assay.

Example 16

The GST-π siRNAs of this invention exhibited reduced off target effects by the passenger strand.

Figure 9:
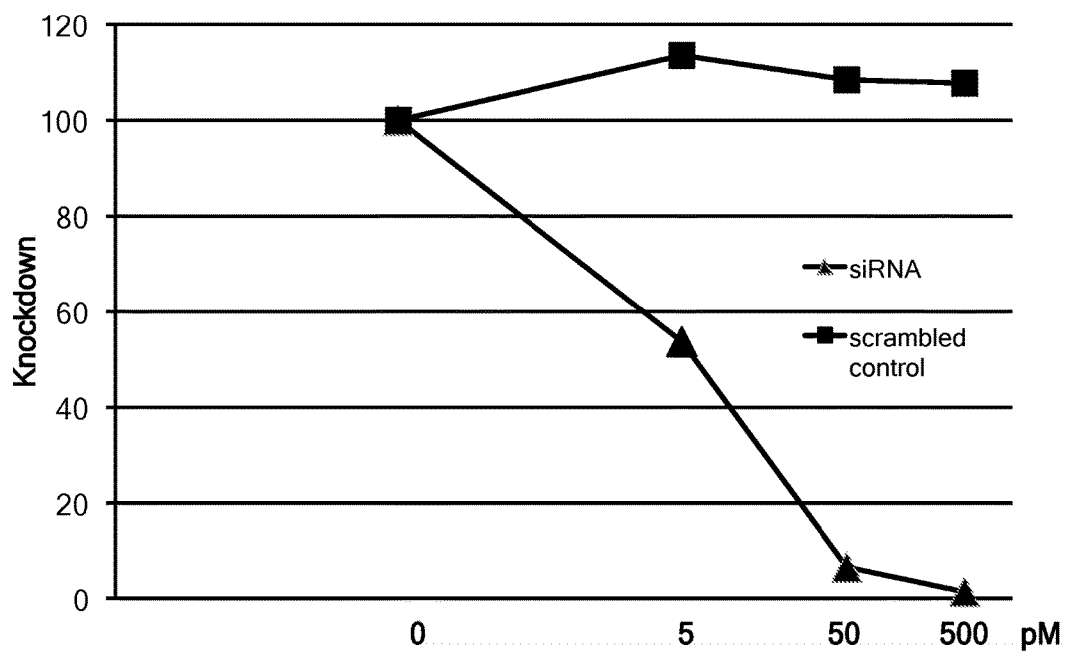
FIG. 9 shows in vitro knockdown for the guide strand of a GST-π siRNA.
Figure 10:
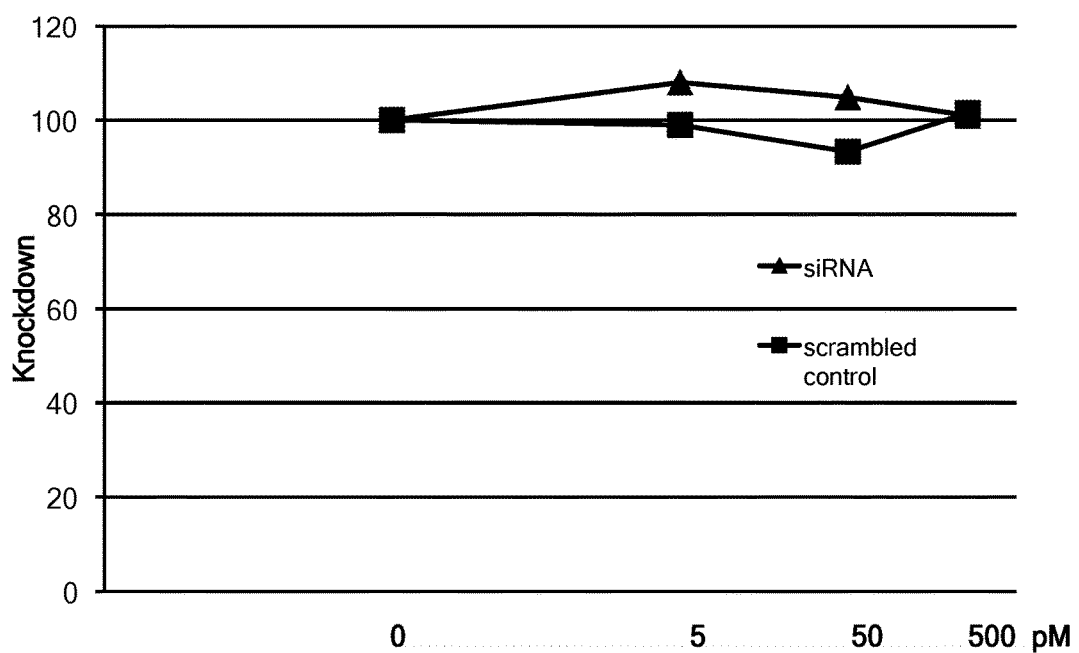
FIG. 10 shows in vitro knockdown for the passenger strand of the GST-π siRNA of FIG. 9.

For the GST-π siRNA (SEQ ID Nos:156 and 182), FIG. 9 shows that in vitro knockdown for the guide strand was approximately exponential, as compared to a control with scrambled sequence that exhibited no effect. The IC50 of this siRNA was measured at 5 pM. FIG. 10 shows in vitro knockdown for the passenger strand of the same GST-π siRNA. As shown in FIG. 10, the passenger strand off target knockdown for the GST-π siRNA was greatly reduced, by more than 100-fold.

Figure 11:
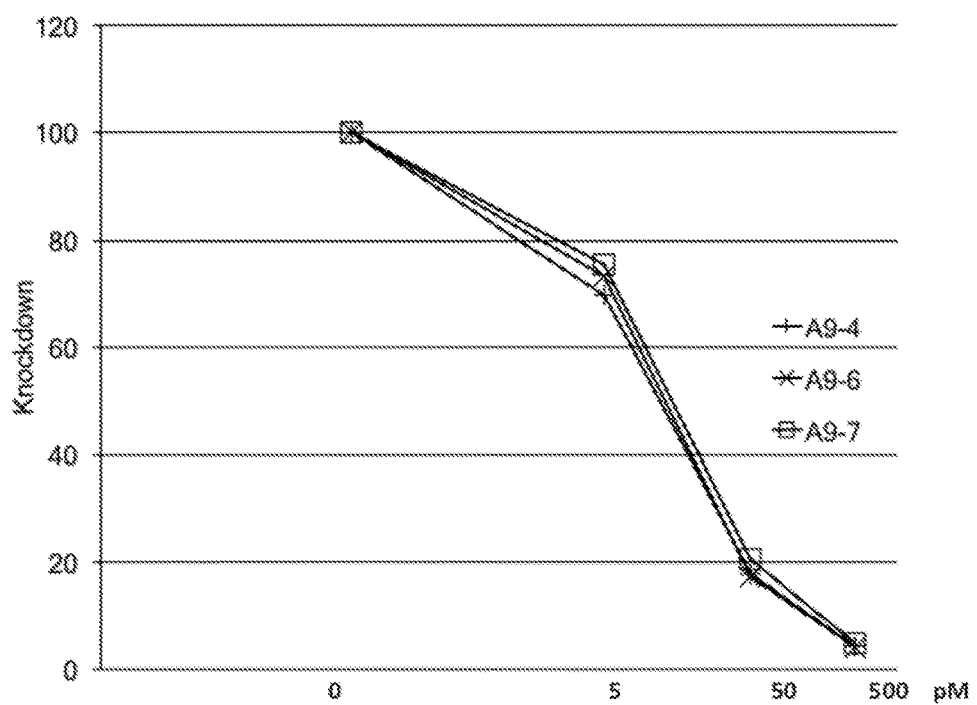
FIG. 11 shows in vitro knockdown for the guide strands of several highly active GST-π siRNAs.
Figure 12:
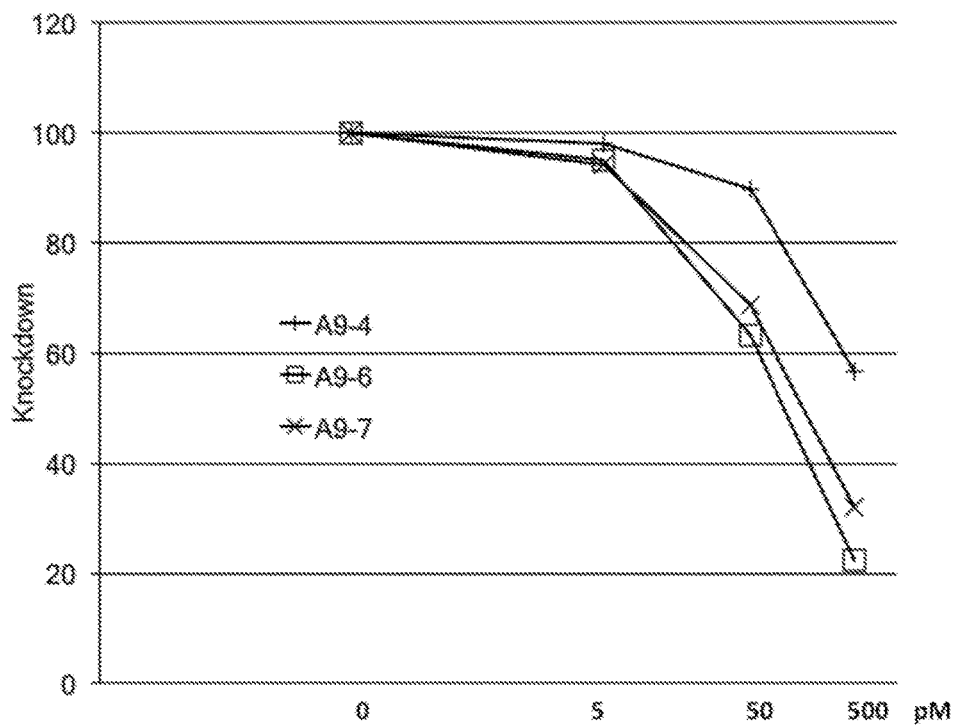
FIG. 12 shows in vitro knockdown for the passenger strand of the GST-π siRNAs of FIG. 11.

For the GST-π siRNAs (SEQ ID Nos:187 and 199), (SEQ ID Nos:189 and 201), and (SEQ ID Nos:190 and 202), FIG. 11 shows that the in vitro knockdowns for the guide strands were approximately exponential. The IC50s of these siRNAs were measured at 6, 7, and 5 pM, respectively. As shown in FIG. 12, the in vitro knockdowns for the passenger strands of these GST-π siRNAs were significantly reduced by at least 10-fold. All of these GST-π siRNAs had deoxynucleotides in the seed region of the duplex region, with no other modifications in the duplex region.

Figure 13:
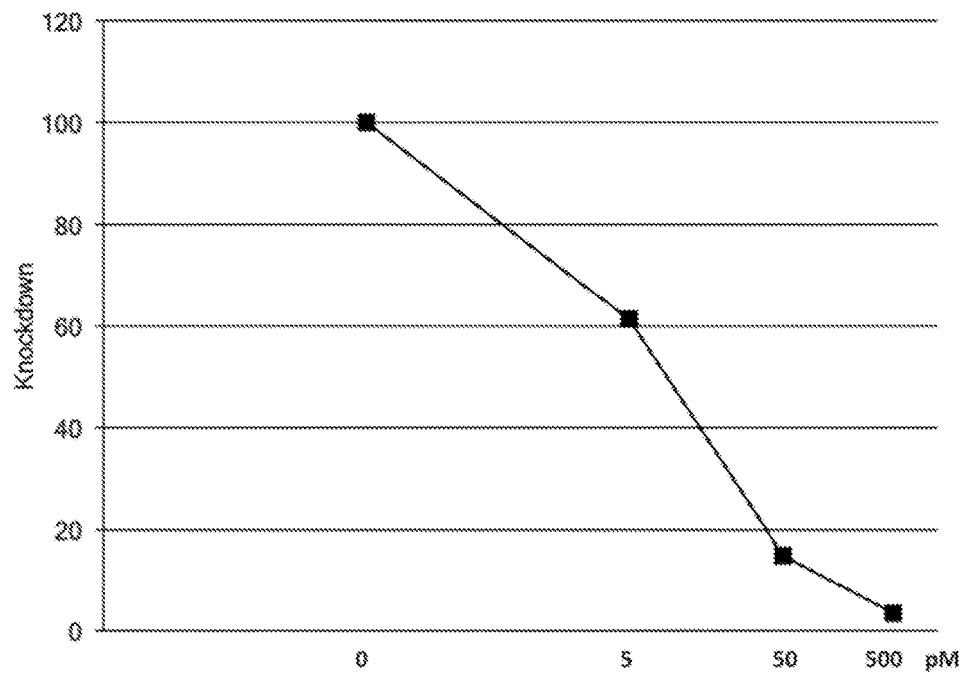
FIG. 13 shows in vitro knockdown for the guide strand of a highly active GST-π siRNA.
Figure 14:
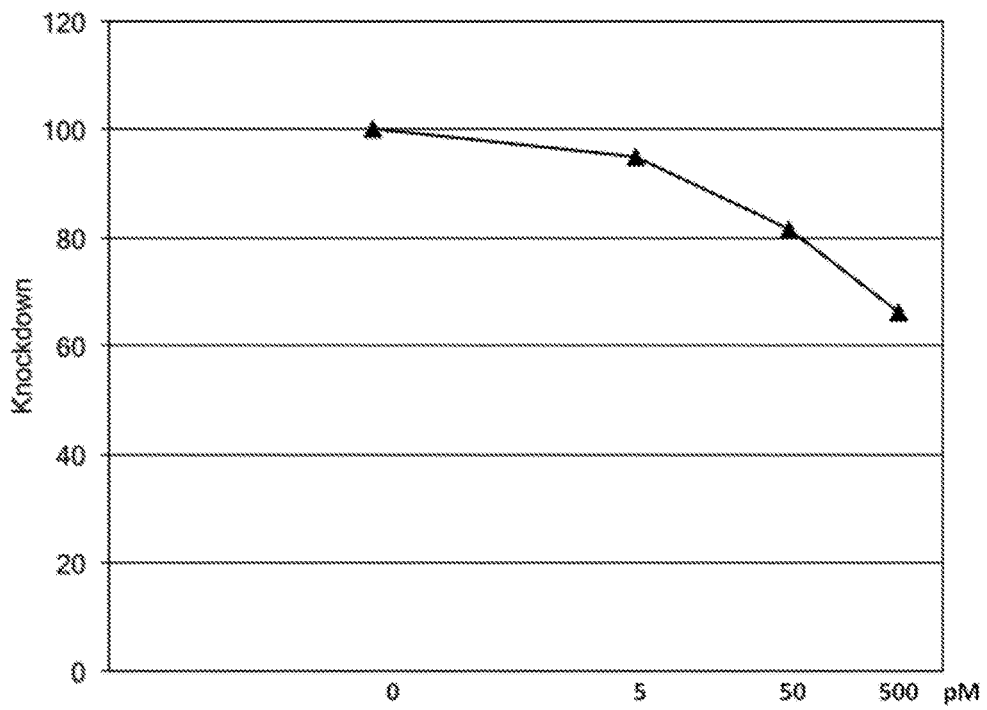
FIG. 14 shows in vitro knockdown for the passenger strand of the GST-π siRNA of FIG. 13.

For the GST-π siRNAs (SEQ ID Nos:217 and 232), FIG. 13 shows that the in vitro knockdown for the guide strand of this highly active GST-π siRNA was approximately exponential. The IC50 of this siRNA was measured at 11 pM. As shown in FIG. 14, the in vitro knockdown for the passenger strand of this GST-π siRNA was significantly reduced by more than 100-fold. This GST-π siRNA had deoxynucleotides in the seed region of the duplex region, with no other modifications in the duplex region.

Off-target effects were determined using the expression reporter plasmid psiCHECK-2, which encodes the *Renilla* luciferase gene. (Dual-Luciferase Reporter Assay System, Promega, Cat#:E1960). The siRNA concentration was typically 50 pM. Protocol: Day 1, HeLa cell seeded at 5 to 7.5×10³/100 ul/well. Day 2, co-transfection with cell confluence about 80%. Day 3, cells harvested for luciferase activity measurement. Luciferase activity was measured using Promega's Luciferase Assay System (E4550), according to manufacturer's protocol.

The psiCHECK-2 vector enabled monitoring of changes in expression of a target gene fused to the reporter gene of *Renilla* luciferase. The siRNA constructs were cloned into the multiple cloning region, and the vector was cotransfected with the siRNA into HeLa cells. If a specific siRNA binds to the target mRNA and initiates the RNAi process, the fused *Renilla* luciferase: construct mRNA will be cleaved and subsequently degraded, decreasing the *Renilla* luciferase signal.

For example, the plasmid inserts for siRNAs with the BU2' structure were as follows:

```
PsiCHECK-2 (F) plasmid insert:
                              SEQ ID NO.: 285
ctcgag gggcaacTGAAGCCTTTTGAGACCCTGcTgTcccag
gcggccgc PsiCHECK-2 (R) plasmid insert:
                              SEQ ID NO.: 286
ctcgag cTgggacagCAGGGTCTCAAAAGGCTTCagTTgccc
gcggccgc
```

Example 17

The GST-π siRNAs of this invention exhibited advantageously reduced miRNA-like off target effects, which are seed-dependent unintended off-target gene silencing.

For the GST-π siRNAs (SEQ ID Nos:156 and 182), (SEQ ID Nos:187 and 199), (SEQ ID Nos:189 and 201), (SEQ ID Nos:190 and 202), and (SEQ ID Nos:217 and 232), off target activity mimicking miRNA was found to be essentially negligible. The seed-dependent unintended off-target gene silencing for these GST-π siRNAs was at least 10-fold to 100-fold less than the on-target activity of the guide strand.

For testing miRNA-related off target effects, one to four repeats of seed-matched target sequences complementary to the entire seed-containing region, positions 1-8 of the 5' end of the antisense strand, but not to the remaining non-seed region, positions 9-21, were introduced into the region corresponding to the 3'UTR of the luciferase mRNA, to determine the efficiency of the seed-dependent unintended off-target effects. Plasmid inserts were used to mimic a miRNA with complete matching in the seed region and mismatches (bulges) in the non-seed region.

For example, the plasmid inserts for siRNAs with the BU2' structure were as follows:

```
PsiCHECK-2 (Fmi1) plasmid insert:
                              SEQ ID NO.: 287
ctcgag gggcaacTCTACGCAAAACAGACCCTGcTgTcccag
gcggccgc PsiCHECK-2 (Fmi2) plasmid insert:
                              SEQ ID NO.: 288
ctcgag gggcaacTCTACGCAAAACAGACCCTGcT
CTACGCAAAACAGACCCTGcT gTcccag gcggccgc PsiCHECK-2 (Fmi3) plasmid insert:
                              SEQ ID NO.: 289
ctcgag gggcaacTCTACGCAAAACAGACCCTGcT
CTACGCAAAACAGACCCTGcT CTACGCAAAACAGACCCTGcT
gTcccag gcggccgc PsiCHECK-2 (Fmi4) plasmid insert:
                              SEQ ID NO.: 290
ctcgag gggcaacTCTACGCAAAACAGACCCTGcT
CTACGCAAAACAGACCCTGcT CTACGCAAAACAGACCCTGcT
CTACGCAAAACAGACCCTGcT gTcccag gcggccgc
```

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A nucleic acid molecule for inhibiting expression of GST-π comprising a sense strand and an antisense strand, wherein the strands form a duplex region, and wherein the antisense strand is UAGGGUCUCAAAAGGCUUCNN SEQ ID NO:157 and the sense strand is GAAGC-CUUUUGAGACCCUANN SEQ ID NO:131, wherein N is selected from the group of A, C, G, U, 2'-OMe-U, a, c, g, u, t, an inverted nucleotide, and a chemically modified nucleotide.

2. The nucleic acid molecule of claim 1, wherein one or more of the nucleotides in the duplex region is chemically-modified.

3. The nucleic acid molecule of claim 2, wherein the chemically-modified nucleotides are selected from 2'-deoxy nucleotides, 2'-O-alkyl substituted nucleotides, 2'-deoxy-2'-fluoro substituted nucleotides, phosphorothioate nucleotides, locked nucleotides, and any combination thereof.

4. The nucleic acid molecule of claim 2, wherein the antisense strand has deoxynucleotides in a plurality of positions, the plurality of positions being one of the following:
   each of positions 4, 6 and 8, from the 5' end of the antisense strand;
   each of positions 3, 5 and 7, from the 5' end of the antisense strand;
   each of positions 1, 3, 5 and 7, from the 5' end of the antisense strand;
   each of positions 3-8, from the 5' end of the antisense strand; or
   each of positions 5-8, from the 5' end of the antisense strand.

5. The nucleic acid molecule of claim 4, wherein the molecule has one or more 2'-deoxy-2'-fluoro substituted nucleotides in the duplex region.

6. The nucleic acid molecule of claim 2, wherein the antisense strand is SEQ ID NO:182 and the sense strand is SEQ ID NO:156.

7. The nucleic acid molecule of claim 2, wherein the antisense strand is SEQ ID NO:180 and the sense strand is SEQ ID NO:154.

8. The nucleic acid molecule of claim 2, wherein the antisense strand is SEQ ID NO:181 and the sense strand is SEQ ID NO:155.

9. The nucleic acid molecule of claim 1, wherein the molecule inhibits expression of GST-π mRNA in A549 cells with an IC50 of less than 50 pM.

10. A pharmaceutical composition comprising the nucleic acid molecule of claim 1 and a pharmaceutically acceptable carrier.

11. The pharmaceutical composition of claim 10, wherein the carrier comprises a lipid molecule or liposome.

12. A vector or cell comprising the nucleic acid molecule of claim 1.

13. A method for treating pancreatic cancer or lung cancer, the method comprising administering to a subject in need a composition of claim 10.

14. A nucleic acid molecule for inhibiting expression of GST-π comprising a sense strand and an antisense strand, wherein the strands form a duplex region, and wherein the antisense strand is ACAGCAGGGUCUCAAAAGGNN SEQ ID NO:195 and the sense strand is CCUUUUGAGAC-CUGCUGUNN SEQ ID NO:183, wherein N is selected from the group of A, C, G, U, 2'-OMe-U, a, c, g, u, t, an inverted nucleotide, and a chemically modified nucleotide.

15. The nucleic acid molecule of claim 14, wherein one or more of the nucleotides in the duplex region is chemically-modified.

16. The nucleic acid molecule of claim 15, wherein the chemically-modified nucleotides are selected from 2'-deoxy nucleotides, 2'-O-alkyl substituted nucleotides, 2'-deoxy-2'-fluoro substituted nucleotides, phosphorothioate nucleotides, locked nucleotides, and any combination thereof.

17. The nucleic acid molecule of claim 15, wherein the antisense strand has deoxynucleotides in a plurality of positions, which plurality of positions are one of the following:
   each of positions 4, 6 and 8, from the 5' end of the antisense strand;
   each of positions 3, 5 and 7, from the 5' end of the antisense strand;
   each of positions 1, 3, 5 and 7, from the 5' end of the antisense strand;
   each of positions 3-8, from the 5' end of the antisense strand; or
   each of positions 5-8, from the 5' end of the antisense strand.

18. The nucleic acid molecule of claim 17, wherein the molecule has one or more 2'-deoxy-2'-fluoro substituted nucleotides in the duplex region.

19. The nucleic acid molecule of claim 14, wherein the molecule inhibits expression of GST-π mRNA in A549 cells with an IC50 of less than 50 pM.

20. A pharmaceutical composition comprising the nucleic acid molecule of claim 14 and a pharmaceutically acceptable carrier.

21. The pharmaceutical composition of claim 20, wherein the carrier is a lipid molecule or liposome.

22. A vector or cell comprising the nucleic acid molecule of claim 14.

23. A method for treating pancreatic cancer or lung cancer, the method comprising administering to a subject in need a composition of claim 20.

* * * * *

SEQUENCE LISTING

```
<160> NUMBER OF SEQ ID NOS: 290

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ucccagaacc agggaggcat t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2
cuuuugagac ccugcuguct t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
cugucccaga accagggagt t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ugucccagaa ccagggaggt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
aagccuuuug agacccugct t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
uugagacccu gcugucccat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 7
uuuugagacc cugcugaccu t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gagacccugc ugucccagat t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
gcuggaagga ggagguggut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuggaaggag gagguggugt t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
ucagggccag agcuggaagt t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 12
ugagacccug cugucccagt t                                           21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
agggccagag cuggaaggat t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
agcuggaagg aggagguggt t                                           21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
agacccugcu gucccagaat t                                           21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gagcuggaag gaggaggugt t                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 17
ugcuguccca gaaccagggt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
cccagaacca gggaggcaat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ccagaaccag ggaggcaagt t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
uuugagaccc ugcuguccct t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
gacccugcug ucccagaact t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 22
gaucagggcc agagcuggat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
agccuuuuga gacccugcut t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
gccuuuugag acccugcugt t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ccuuuugaga cccugcugut t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
cgccuuuuga gacccugcat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic

```
            oligonucleotide
<220> FEATURE:
<223> OTHER INFORMATION: Description of Combined DNA/RNA Molecule:
      Synthetic oligonucleotide

<400> SEQUENCE: 27
ccuacaccgu ggucuauuut t                                             21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
ugugggagac cagaucucct t                                             21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
gcgggaggca gaguuugcct t                                             21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
ccuuucucca ggaccaauat t                                             21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
acccugcugu cccagaacct t                                             21

<210> SEQ ID NO 32
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
ggucuauuuc ccaguucgat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
cccuggugga cauggugaat t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
acaucucccu caucuacact t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
gcaaggauga cuaugugaat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ccuucgcuga cuacaaccut t                                              21

<210> SEQ ID NO 37
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
cuggcagauc agggccagat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
gacggagacc ucacccugut t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cgggcaagga ugacuaugut t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
cuuuugagac ccugcuguat t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gagcuggaag gaggagguat t                                              21

<210> SEQ ID NO 42
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
acccugcugu cccagaacat t                                                 21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
ugcuguccca gaaccaggat t                                                 21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
agccuuuuga gacccugcat t                                                 21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ccuuuugaga cccugcugat t                                                 21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
ugaagccuuu ugagaccccut t                                                21

<210> SEQ ID NO 47
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
acugaagccu uuugagacct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
aggaugacua ugugaaggct t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
ggaugacuau gugaaggcat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
gaugacuaug ugaaggcact t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cucccucauc uacaccaact t                                              21

<210> SEQ ID NO 52
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
gaagccuuuu gagacccugt t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ucucccucau cuacaccaat t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ccucaucuac accaacuaut t                                              21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
cccucaucua caccaacuat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
caacugaagc cuuuugagat t                                              21
```

```
<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
aacugaagcc uuuugagact t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
cugaagccuu uugagaccct t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
ucccucaucu acaccaacut t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
gcucccucau cuacaccaat t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
gaagccuuuu gagacccuat t                                              21
```

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 62
acugaagccu uuugagacat t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 63
cucccucauc uacaccaaat t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 64
ccucaucuac accaacuaat t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 65
accaauaaaa uuucuaagat t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 66
ugccucccug guucugggac a                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
gacagcaggg ucucaaaagg c                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
cucccugguu cugggacagc a                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
ccucccuggu ucugggacag c                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
gcagggucuc aaaaggcuuc a                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
ugggacagca gggucucaaa a                                             21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
ggacagcagg gucucaaaag g                                             21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ucugggacag cagggucuca a                                             21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
accaccuccu ccuuccagct c                                             21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
caccaccucc uccuuccagc t                                             21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
cuuccagcuc uggcccugat c                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
cugggacagc agggucucaa a                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
uccuuccagc ucuggcccug a                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ccaccuccuc cuuccagcuc t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
uucugggaca gcagggucuc a                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
caccuccucc uuccagcuct g    21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cccugguucu gggacagcag g    21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
uugccucccu gguucuggga c    21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
cuugccuccc ugguucuggg a    21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
gggacagcag ggucucaaaa g    21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
guucugggac agcagggucu c                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
uccagcucug gcccugauct g                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
agcagggucu caaaaggcut c                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
cagcagdguc ucaaaaggct t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
acagcagggu cucaaaaggc t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 91 ugcaggucu caaaaggcgt c            21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
aaauagacca cgguguaggg c            21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
ggagaucugg ucucccacaa t            21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
ggcaaacucu gccucccgct c            21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
uauugguccu ggagaaagga a            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 96
gguucuggga cagcaggguc t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ucgaacuggg aaauagacca c                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
uucaccaugu ccaccagggc t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
guguagauga gggagaugua t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
uucacauagu cauccuugcc c                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 101
agguuguagu cagcgaagga g                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
ucuggcccug aucugccagc a                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
acagggugag gucuccgucc t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
acauagucau ccuugcccgc c                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
uacagcaggg ucucaaaagg c                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 106
uaccuccucc uuccagcuct g                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
uguucuggga cagcaggguc t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
uccugguucu gggacagcag g                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
ugcagggucu caaaaggcut c                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
ucagcagggu cucaaaaggc t                                              21

<210> SEQ ID NO 111
<211> LENGTH: 21
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
agggucucaa aaggcuucag t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ggucucaaaa ggcuucagut g                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
gccuucacau agucauccut g                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ugccuucaca uagucaucct t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gugccuucac auagucaucc t                                              21

<210> SEQ ID NO 116
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
guugguguag augagggaga t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cagggucuca aaaggcuuca g                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
uugguguaga ugagggagat g                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
auaguuggug uagaugaggg a                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
uaguuggugu agaugaggga g                                              21

<210> SEQ ID NO 121
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
ucucaaaagg cuucaguugc c                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gucucaaaag gcuucaguug c                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
gggucucaaa aggcuucagt t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
aguuggugua gaugagggag a                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
uugguguaga ugagggagct g                                              21

<210> SEQ ID NO 126
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
uagggucuca aaaggcuuca g                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
ugucucaaaa ggcuucagut g                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
uuugguguag augagggaga t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
uuaguuggug uagaugaggg a                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
ucuuagaaau uuuauugguc c                                              21

<210> SEQ ID NO 131
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 131
gaagccuuuu gagacccuan n                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 132
gaagccuuuu gagacccuau u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 133
gaagccuuuu gagacccuau u                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 134
gaagccuuuu gagacccuau u                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 135
gaagccuuuu gagacccuau u                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 136
gaagccuuuu gagacccuau u                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 137
gaagccuuuu gagacccuau u                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 138
gaagccuuuu gagacccuau u                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 139
gaagccuuuu gagacccuau u                                              21

<210> SEQ ID NO 140
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 140
gaagccuuuu gagacccuau u                                          21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 141
gaagccuuuu gagacccuau u                                          21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
gaagccuuuu gagacccuat t                                          21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 143
gaagccuuuu gagacccuau u                                          21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 144
gaagccuuuu gagacccuau u                                          21
```

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 145
gaagccuuuu gagacccuau u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 146
gaagccuuuu gagacccuau u                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 147
gaagccuuuu gagacccuau u                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-deoxy-2'-fluoro-nucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 148
gaagccuuuu gagacccuau u                                                    21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 149
gaagccuuuu gagacccuau u                                                    21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 150
gaagccuuuu gagacccuau u                                                    21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 151
gaagccuuuu gagacccuau u                                                    21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 152
gaagccuuuu gagacccuau u                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 153
gaagccuuuu gagacccuau u                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 154
gaagccuuuu gagacccuau u                                              21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base

```
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 155
gaagccuuuu gagacccuau u                                              21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 156
gaagccuuuu gagacccuau u                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 157
uagggucuca aaaggcuucn n                                              21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 158
```

-continued uagggucuca aaaggcuucu u                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 159
uagggucuca aaaggcuucu u                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 160
uagggucuca aaaggcuucu u                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base

```
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 161
uagggucuca aaaggcuucu u                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 162
uagggucuca aaaggcuucu u                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 163
uagggucuca aaaggcuucu u                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 164
uagggucuca aaaggcuucu u                                          21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 165
uagggucuca aaaggcuucu u                                          21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 166
uagggucuca aaaggcuucu u                                          21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide

```
<220> FEATURE:
<221> NAME/KEY: modified_base
<222> LOCATION: (20)..(21)
<223> OTHER INFORMATION: 2'-OMe-nucleotide

<400> SEQUENCE: 167
uagggucuca aaaggcuucu u                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 168
uagggucuca aaaggcuucu u                                              21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 169
uagggucuca aaaggcuucu u                                              21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 170
uagggucuca aaaggcuucu u                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 171
uagggucuca aaaggcuucu u                                              21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Phosphorothioate linkage
<220> FEATURE:
<221> NAME/KEY: modified_base
<222> LOCATION: (20)..(21)
<223> OTHER INFORMATION: 2'-OMe-nucleotide

<400> SEQUENCE: 172
uagggucuca aaaggcuucu u                                              21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 173
uagggucuca aaaggcuucu u                                              21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
<222> LOCATION: (11)..(12)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 174
uagggucuca aaaggcuucu u                                              21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 175
uagggucuca aaaggcuucu u                                              21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 176
uagggucuca aaaggcuucu u                                          21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 177
uagggucuca aaaggcuucu u                                          21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 178
uagggucuca aaaggcuucu u                                          21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
```

```
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 179
uagggucuca aaaggcuucu u                                       21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 180
uagggucuca aaaggcuucu u                                       21

<210> SEQ ID NO 181
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 181
uagggucuca aaaggcuucu u                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 182
uagggucuca aaaggcuucu u                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 183
ccuuuugaga cccugcugun n                                              21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 184
ccucaucuac accaacuauu u                                              21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 185
ccucaucuac accaacuauu u                                              21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 186
ccucaucuac accaacuauu u                                              21

<210> SEQ ID NO 187
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 187
ccucaucuac accaacuauu u                                                 21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 188
ccucaucuac accaacuauu u                                                 21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 189
ccucaucuac accaacuauu u                                                 21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 190
ccucaucuac accaacuauu u                                                 21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 191
ccucaucuac accaacuauu u                                                 21
```

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 192
ccucaucuac accaacuauu u                                              21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 193
ccucaucuac accaacuauu u                                              21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 194
ccucaucuac accaacuauu u                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 195
acagcagggu cucaaaaggn n                                                    21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 196
auaguuggug uagaugaggu u                                                    21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 197
auaguuggug uagaugaggu u                                                    21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 198
auaguuggug uagaugaggu u                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 199
auaguuggug uagaugaggu u                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 200
auaguuggug uagaugaggu u                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 201
auaguuggug uagaugaggu u                                              21
```

```
<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 202
auaguuggug uagaugaggu u                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 203
auaguuggug uagaugaggu u                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 204
auaguuggug uagaugaggu u                                              21

<210> SEQ ID NO 205
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 205
auaguuggug uagaugaggu u                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 206
auaguuggug uagaugaggu u                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 207
```
gaugacuaug ugaaggcacn n                    21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 208
ggaugacuau gugaaggcau u                    21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 209
ggaugacuau gugaaggcau u                    21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 210
ggaugacuau gugaaggcau u                    21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 211
ggaugacuau gugaaggcau u                    21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (20)..(21)
<223> OTHER INFORMATION: 2'-OMe-nucleotide

<400> SEQUENCE: 212
ggaugacuau gugaaggcau u                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 213
ggaugacuau gugaaggcau u                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 214
ggaugacuau gugaaggcau u                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 215
ggaugacuau gugaaggcau u                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 216
ggaugacuau gugaaggcau u                                              21

<210> SEQ ID NO 217
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 217
ggaugacuau gugaaggcau u                                          21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 218
ggaugacuau gugaaggcau u                                          21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-deoxy-2'-fluoro-nucleotide
<220> FEATURE:
<221> NAME/KEY: modified_base
<222> LOCATION: (13)..(13)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 219
ggaugacuau gugaaggcau u                                          21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
       oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 220
ggaugacuau gugaaggcau u                                           21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 221
ggaugacuau gugaaggcau u                                           21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 222
gugccuucac auagucaucn n                                           21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 223
ugccuucaca uagucauccu u                                           21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
          oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 224
ugccuucaca uagucauccu u                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 225
ugccuucaca uagucauccu u                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 226
ugccuucaca uagucauccu u                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 227
ugccuucaca uagucauccu u                                                   21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 228
ugccuucaca uagucauccu u                                                   21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 229
ugccuucaca uagucauccu u                                                   21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base

```
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 230
ugccuucaca uagucauccu u                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 231
ugccuucaca uagucauccu u                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 232
ugccuucaca uagucauccu u                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
```

```
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 233
ugccuucaca uagucauccu u                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 234
ugccuucaca uagucauccu u                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 235
ugccuucaca uagucauccu u                                              21

<210> SEQ ID NO 236
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 236
ugccuucaca uagucauccu u                                              21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 237
gaagccuuuu gagacccugn n                                              21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 238
gaagccuuuu gagacccugu u                                              21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 239
```

```
gaagccuuuu gagacccugu u                                              21
```

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 240

```
gaagccuuuu gagacccugu u                                              21
```

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 241

```
gaagccuuuu gagacccugu u                                              21
```

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 242

```
gaagccuuuu gagacccugu u                                              21
```

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 243

```
gaagccuuuu gagacccugu u                                              21
```

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: 2'-OMe-nucleotide

<400> SEQUENCE: 244
gaagccuuuu gagacccugu u                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 245
gaagccuuuu gagacccugu u                                              21

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 246
gaagccuuuu gagacccugu u                                              21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 247
gaagccuuuu gagacccugu u                                              21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
```

```
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 248
gaagccuuuu gagacccugu u                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 249
cagggucuca aaaggcuucn n                                              21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 250
cagggucuca aaaggcuucu u                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide
```

<400> SEQUENCE: 251
cagggucuca aaaggcuucu u                                          21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 252
cagggucuca aaaggcuucu u                                          21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 253
cagggucuca aaaggcuucu u                                          21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide

```
<220> FEATURE:
<221> NAME/KEY: modified_base
<222> LOCATION: (20)..(21)
<223> OTHER INFORMATION: 2'-OMe-nucleotide

<400> SEQUENCE: 254
cagggucuca aaaggcuucu u                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 255
cagggucuca aaaggcuucu u                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 256
cagggucuca aaaggcuucu u                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
cagggucuca aaaggcuucu u                                              21

<210> SEQ ID NO 258
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 258
cagggucuca aaaggcuucu u                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 259
cagggucuca aaaggcuucu u                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
```

<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 260
cagggucuca aaaggcuucu u                                           21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 261
ccucaucuac accaacuaun n                                           21

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 262
ccucaucuac accaacuauu u                                           21

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 263
ccucaucuac accaacuauu u                                           21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 264

-continued ccucaucuac accaacuauu u                                             21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 265
ccucaucuac accaacuauu u                                             21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 266
ccucaucuac accaacuauu u                                             21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 267
ccucaucuac accaacuauu u                                             21

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 268
ccucaucuac accaacuauu u                                             21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (20)..(21)
<223> OTHER INFORMATION: 2'-OMe-nucleotide

<400> SEQUENCE: 269
ccucaucuac accaacuauu u                                              21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 270
ccucaucuac accaacuauu u                                              21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 271
ccucaucuac accaacuauu u                                              21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 272
ccucaucuac accaacuauu u                                              21
```

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 273
auaguuggug uagaugaggn n                                              21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 274
auaguuggug uagaugaggu u                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 275
auaguuggug uagaugaggu u                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<221> NAME/KEY: modified_base

```
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 276
auaguuggug uagaugaggu u                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 277
auaguuggug uagaugaggu u                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 278
auaguuggug uagaugaggu u                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
```

```
<221> NAME/KEY: modified_base
<222> LOCATION: (20)..(21)
<223> OTHER INFORMATION: 2'-OMe-nucleotide

<400> SEQUENCE: 279
auaguuggug uagaugaggu u                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 280
auaguuggug uagaugaggu u                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 281
auaguuggug uagaugaggu u                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide
```

<400> SEQUENCE: 282
auaguuggug uagaugaggu u                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 283
auaguuggug uagaugaggu u                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 284
auaguuggug uagaugaggu u                                              21

<210> SEQ ID NO 285
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 285
ctcgaggggc aactgaagcc ttttgagacc ctgctgtccc aggcggccgc        50

<210> SEQ ID NO 286
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
ctcgagctgg acagcaggg tctcaaaagg cttcagttgc ccgcggccgc         50

<210> SEQ ID NO 287
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
ctcgaggggc aactctacgc aaaacagacc ctgctgtccc aggcggccgc        50

<210> SEQ ID NO 288
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ctcgaggggc aactctacgc aaaacagacc ctgctctacg caaaacagac cctgctgtcc    60
caggcggccg c                                                         71

<210> SEQ ID NO 289
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
ctcgaggggc aactctacgc aaaacagacc ctgctctacg caaaacagac cctgctctac    60
gcaaaacaga ccctgctgtc ccaggcggcc gc                                  92

<210> SEQ ID NO 290
<211> LENGTH: 113
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ctcgaggggc aactctacgc aaaacagacc ctgctctacg caaaacagac cctgctctac      60
gcaaaacaga ccctgctcta cgcaaaacag accctgctgt cccaggcggc cgc            113
```